(12) United States Patent
Francois

(10) Patent No.: US 9,271,899 B2
(45) Date of Patent: Mar. 1, 2016

(54) METHODS, ARTICLES AND KITS FOR ALLERGIC DESENSITIZATION, VIA THE ORAL MUCOSA

(75) Inventor: Cedric Francois, Louisville, KY (US)

(73) Assignee: Allovate, LLC, New York, NY (US)

( * ) Notice: Subject to any disclaimer, the term of this patent is extended or adjusted under 35 U.S.C. 154(b) by 0 days.

(21) Appl. No.: 13/695,169

(22) PCT Filed: May 2, 2011

(86) PCT No.: PCT/US2011/034731
§ 371 (c)(1),
(2), (4) Date: Feb. 1, 2013

(87) PCT Pub. No.: WO2011/137420
PCT Pub. Date: Nov. 3, 2011

(65) Prior Publication Data
US 2013/0149670 A1    Jun. 13, 2013

Related U.S. Application Data

(60) Provisional application No. 61/329,719, filed on Apr. 30, 2010.

(51) Int. Cl.
| | |
|---|---|
| *A61J 7/00* | (2006.01) |
| *A61C 19/06* | (2006.01) |
| *A61K 39/35* | (2006.01) |
| *A61K 8/02* | (2006.01) |
| *A61K 8/97* | (2006.01) |
| *A61K 8/98* | (2006.01) |
| *A61Q 11/00* | (2006.01) |

(52) U.S. Cl.
CPC ............. *A61J 7/0076* (2013.01); *A61C 19/063* (2013.01); *A61K 8/0208* (2013.01); *A61K 8/975* (2013.01); *A61K 8/987* (2013.01); *A61K 39/35* (2013.01); *A61Q 11/00* (2013.01)

(58) Field of Classification Search
None
See application file for complete search history.

(56) References Cited

U.S. PATENT DOCUMENTS

| | | | |
|---|---|---|---|
| 6,042,812 A | 3/2000 | Sanker et al. | |
| 6,113,887 A | 9/2000 | Mori et al. | |
| 6,780,416 B1 * | 8/2004 | Spertini | 424/185.1 |
| 6,821,507 B2 | 11/2004 | Glandorf et al. | |
| 7,300,645 B2 | 11/2007 | Takatsuka et al. | |
| 2004/0241107 A1 * | 12/2004 | Burzynski et al. | 424/49 |
| 2006/0171968 A1 * | 8/2006 | Brimnes et al. | 424/275.1 |
| 2007/0031539 A1 | 2/2007 | Carlton, Jr. | |
| 2007/0110673 A1 * | 5/2007 | Spertini et al. | 424/9.8 |
| 2007/0219153 A1 * | 9/2007 | Kandimalla et al. | 514/44 |
| 2008/0152695 A1 | 6/2008 | Clark et al. | |
| 2008/0302682 A1 | 12/2008 | Engstrom et al. | |
| 2009/0214597 A1 | 8/2009 | Moldt et al. | |
| 2010/0018540 A1 | 1/2010 | Doolittle et al. | |
| 2011/0142867 A1 * | 6/2011 | Larche et al. | 424/185.1 |

FOREIGN PATENT DOCUMENTS

| | | |
|---|---|---|
| WO | 9301213 | 1/1993 |
| WO | 2008098749 A2 | 8/2008 |
| WO | 2008156704 A2 | 12/2008 |
| WO | 2010128364 A1 | 11/2010 |

OTHER PUBLICATIONS

Directions for use of Listerine Total Care Anticavity Mouthwash. <http://www.listerine.com/products/total-care-fresh-mint-anticavity-mouthwash> (Jun. 2, 2014).*
Sridhara et al. (Asian Pacific Journal of Allergy and Immunology (1992) 10:33-38).*
Asturias J.A. et al., Tolerance and immunological changes of chemically modified allergen vaccine of Parietaria judaica in accelerated schedules, Clinical and Experimental Immunology, Dec. 5, 2006, 147:491-496, 147, British Society for Immunology.
Calderon M., et al., Specific Immunotherapy with High Dose SQ Standardized Grass Allergen Tablets was Safe and Well Tolerated, J. Investig Alergol Clin Immunol, 2006, 16(6)338-344.
Didier A., et al., Optimal dose, efficacy, and safety of once-daily sublingual immunotherapy with a 5-grass pollen tablet for seasonal allergic rhinitis, American Academy of Allergy, Asthma & Immunology, 2007, pp. 1338-1345; DOI:10.1016/j.jaci.2007.07.046.
Frati F., et al., Development of a sublingual allergy vaccine for grass pollinosis, Drug Design, Development and Therapy, 2010(4), pp. 99-105.
Futamura N., et al., Characterization of genes for novel thaumatin-like proteins in Cryptomeria japonica, Tree Physiology, Oct. 3, 2005; (26)51-62; Heron Publishing, Victoria, Canada.
Futamura N., et al., Isolation and Characterization of cDNAs that Encode Homologs of a Pathogenesis-related Protein Allergen from Cryptornecia japonica, Biosci. Biotechnol. Biochem., 66 (11), 2495-2500, 2002.
Committee for Medicinal Products for Human Use (CHMP), Guideline on the Clinical Development of Products for Specific Immunotherapy for the Treatment of Allergic Diseases, European Medicines Agency, Nov. 20, 2008, pp. 1-13; London, UK.
Ivanciuc O., et al., SDAP: database and computational tools for allergenic proteins, Nucleic Acids Research, 2003, vol. 31, No. 1, pp. 359-362; DOI: 10.1093/nar/gkg010.
Kamdar T., et al., Immunotherapy in food allergy, Immunotherapy, May 1, 2010; 2(3):329-338; DOI:10.2217/imt.10.15.
Kleine-Tebbe J., et al., Safety of a SQ-standardised grass allergen tablet for sublingual immunotherapy: a randomized, placebo-controlled trial, Allergy, 2006, 61:181-184; Blackwell Munksgaard; DOI: 10.1111/j.1398-9995.2006.00959.x.

(Continued)

*Primary Examiner* — David J Blanchard
*Assistant Examiner* — Garen Gotfredson
(74) *Attorney, Agent, or Firm* — Dinsmore & Shohl

(57) ABSTRACT

Compositions and methods of use for desensitizing a subject to an allergen via regions of the oral mucosa are provided.

20 Claims, No Drawings

(56) References Cited

OTHER PUBLICATIONS

Lindbo, J., High-efficiency protein expression in plants from agroinfection-compatible Tobacco mosaic virus expression vectors, BMC Biotechnology, 2007(7):52; DOI:10.1186/1472-6750-7-52; http://www.biomedcentral.com/1472-6750/7/52.

Lizaso M.T., et al., Biological standardization and maximum tolerated dose estimation of an Alternaria alternata allergenic extract, J. Investig Allergol Clin Immunol 2006; vol. 16(2): 94-103.

Matsumura D. et al., Detection of New Antigenic Proteins in Japanese Cedar Pollen, Biol. Pharm. Bull 2006; 29(6) 1162-1166, Pharmaceutical Society of Japan.

Namba M., et al., Molecular cloning of the second major allergen, Cry j II, from Japanese cedar pollen, Federation of European Biochemical Societies (FEBS) FEBS Letters 353 (1994): 124-128.

Okubo K., et al., Allergen Immunotherapy for Allergic Rhinitis, J Nippon Med Sch. 2010: 77(6)285-289.

Okubo K., et al., Sublingual Immunotherapy for Japanese Cedar Pollinosis, Allergology International, 2009;58(2):149-154; DOI: 10.2332/allergolint.08-RAI-0072.

Tong JC, et al., Allergen Atlas; a comprehensive knowledge center and analysis resource for allergen information, Bioinformatics, 2009, vol. 25(7); 979-980; DOI: 10.1093/bioinformatics/btp077.

Tsunematsu M., et al., Effect of Cry-consensus Peptide, a Novel Recombinant Peptide for Immunotherapy of Japanese Cedar Pollinosis, on an Experimental Allergic Rhinitis Model in B10.S Mice, Allergology International, 2007, 56(4):465-472: DOI: 10.2332/allergolint.O-07-495.

Yokozeki H., et al., Japanese Cedar Pollen as an Exacerbation Factor in Atopic Dermatitis: Results of Atopy Patch Testing and Histological Examination, Acta Derm Venereol, 2006; 86: 148-151; DOI: 10.2340/00015555-0020.

Ashkenazi, M. D.M.D., et al., Self-Reported Compliance with Preventive Measures Among Regularly Attending Pediatric Patients, Journal of Dental Education, Feb. 2007, pp. 287-295.

MacFarlane, Tatiana V. et al., Mouthwash Use in General Population: Results from Adult Dental Health Survey in Grampian, Scotland, Journal of Oral & Maxillofacial Research Oct.-Dec. 2010 vol. 1, No. 4, e2, pp. 1-9.

\* cited by examiner

SEQUENCE LISTING

<160> NUMBER OF SEQ ID NOS: 1

<210> SEQ ID NO 1
<211> LENGTH: 105
<212> TYPE: PRT
<213> ORGANISM: artificial

-continued

```
<220> FEATURE:
<223> OTHER INFORMATION: Cry-consensus peptide with six major human
      T-cell epitopes

<400> SEQUENCE: 1

Met Lys Val Thr Val Ala Phe Asn Gln Phe Gly Pro Asn Arg Arg Val
1               5                   10                  15

Phe Ile Lys Arg Val Ser Asn Val Ile Ile His Gly Arg Arg Ile Asp
            20                  25                  30

Ile Phe Ala Ser Lys Asn Phe His Leu Gln Lys Asn Thr Ile Gly Thr
        35                  40                  45

Gly Arg Arg Trp Lys Asn Asn Arg Ile Trp Leu Gln Phe Ala Lys Leu
    50                  55                  60

Thr Gly Phe Thr Leu Met Gly Arg Arg Leu Lys Met Pro Met Tyr Ile
65                  70                  75                  80

Ala Gly Tyr Lys Thr Phe Asp Gly Arg Arg Val Asp Gly Ile Ile Ala
                85                  90                  95

Ala Tyr Gln Asn Pro Ala Ser Trp Lys
            100                 105
```

METHODS, ARTICLES AND KITS FOR ALLERGIC DESENSITIZATION, VIA THE ORAL MUCOSA

The present application claims priority under 35 U.S.C. §119(e) to U.S. Provisional Application Ser. No. 61/329,719 filed Apr. 30, 2010.

The invention relates to allergic immunotherapy targeting regions of the oral mucosa, such as those having a high dendritic to mast cell ratio, in particular targeting the vestibular mucosa. In some aspects, the invention relates to delivery articles and dosing forms which, for example, increase contact time and efficacy with an enhanced safety profile over sublingual immunotherapy.

Chronic allergic hypersensitivity disorder results from a combination of genetic susceptibility, failure of the immune system to properly prime during a critical stage in infancy, and subsequent repeated exposure to a causative allergen. The sufferer develops a hyperimmune response to the allergen that manifests clinically as allergic inflammation at the site of contact, underpinned by antigen presenting cells, Th cells, effector cells such as mast cells, and generally IgE mediated production of cytokines. The incidence of IgE-mediated allergic disease is spiking in industrialized Western cultures with recent estimates for total percent of the population afflicted in the United States running as high as about 20%. In addition to the substantial loss realized in reduced productivity and a compromised quality of life, anaphylactic and severe asthmatic episodes may actually be life-threatening.

The clinical manifestation of a hyperallergenic immune system often begins very early in life. Medical investigators have identified a syndromic profile in some individuals referred to as "atopic syndrome," which includes a strong genetic predisposition reflected in multiple first and second degree familial links, coupled with an early clinical onset of the "allergic triad" of eczema, hay fever and asthma. Acute immune system response manifest as, for example, food allergies and other abnormal immune responses are also very common in this population. Despite the genetic contribution to the atopic phenotype, it is also clear that environment plays a significant if not critical role in expression.

Central to treatment approaches is the "hygienic hypothesis" of allergic etiology. According to this paradigm, an overly sterile environment during a critical stage in development of the immune system leads to aborted maturation, hypersensitivity to allergens, over production of IgE and ultimately cytokines, and clinical symptoms of allergy. At birth, human infants possess a Th2 biased immune system as an artifact of the gestational period. In normal circumstances, the bias switches after about three to six months toward Th1. A proper Th1/Th2 balance results in the capacity for developing immune tolerance to environmental allergens. The modern theory of allergy is that it reflects an abnormally persistent Th2 weighted imbalance, and immunologists have therefore focused long-term treatment on methods for redirecting the Th2 toward a Th1 response. In treatment approaches aimed at treating individuals with established allergic hypersensitivity, medical clinicians use exposure to allergen to drive up the Th1 response.

Current therapy for individuals suffering from the symptoms of a hyperallergenic immune system includes medication such as antihistamines, leukotriene inhibitors and corticosteroids, and allergic immunotherapy (AIP). Allergenic immunization has been known since the early part of the 20$^{th}$ century and has the goal of inducing allergen-specific tolerance in individuals exhibiting allergen-specific clinical symptoms. Subcutaneous immunotherapy, commonly referred to as SCIT, has been a treatment of choice for more than half a century. SCIT is indicated where patients have a history of allergic symptoms on exposure to an offending allergen in addition to evidence of an inappropriate IgE response to that allergen. SCIT has been confirmed to induce the desired immune response shift from a Th2 to Th1 bias and also to induce T (regulators) which down-regulate Th2 response. SCIT has been demonstrated to offer significant relief from symptoms of, for example, pollen and ragweed allergy, insect venom allergy, and asthma secondary to allergic rhinitis. Drawbacks, however, include expense, inconvenience, and the potential for induction of potentially fatal systemic allergic reactions requiring administration of epinephrine and a need for clinical facilities and administration by highly trained technicians to avoid anaphylaxis.

More recently, sublingual immunotherapy (SLIT), a therapy that evolved as part of a maintenance adjunct with SCIT, has received considerable research and clinical attention. SLIT provides cheaper more convenient therapeutic potential, possesses a strong safety profile with little chance of a systemic response, and several recent large scale studies confirm the efficacy and validate the underpinning theoretical model. Generally efficacy of SLIT is based on the observation that the oral mucosa appears particularly primed in mammals for development of allergenic tolerance and possesses specialized cells which function to achieve this. Antigen presenting cells (APC) are the initiators of the immune response and are present in the surface of tissues in communication with the environment. APCs capture and present allergens to T-cells, which in turn transport them to a proximal draining lymph node for recognition and processing by effector cells including mast cells. Mast cells are the tissue based non-circulating effector cells which release mediators such as IgE responsible for the ultimate inflammatory response. Among APCs, dendritic cells, including the specialized Langerhans cells, are considered the most important inducers of tolerance to allergens through their interaction with T-cells.

The mouth provides a major intake orifice for potential allergens and the presence of dendritic cells in the oral mucosa are believed to play a role in the enhanced development of oral immune tolerance in humans. The distribution of dendritic cells, in particular Langerhans cells, in the oral mucosa and the enhanced development of oral tolerance, taken with the obvious advantages and conveniences associated non-invasive therapies in general, provided the impetus to explore the oral mucosa as an alternative site for targeted allergen immunotherapy.

SLIT is typically administered as droplets or lozenges, or in tablet form intended to be held under the tongue for a few minutes and then swallowed. Optimal dosing regimens depend on the specific target allergen, the age of the sufferer, and the strength of the abnormal response sought to be ameliorated. SLIT appears to influence T and B-cell response similarly to SCIT but appears more limited. A significant drawback appears to be that efficacy is highly dependent on exposure time to the tissue surface, whereas the most commonly employed dosage forms are subject to rapid egress from the oral cavity and ultimately digestion. Further, dosage forms designed for sustained exposure, for example slow-dissolving lozenges held beneath the tongue, are associated with development of sublingual edema, most likely due to the presence of mast cells located in the glands of the sublingual oral mucosa.

It was recently discovered, however, that other regions of the oral mucosa possess a dendritic cell and mast cell distribution profile that may be more suited for safe and effective oral immunotherapy. (See Allam et al. *Allergy* 2008: 63:

720-727, the entire disclosure of which is incorporated herein by this reference). According to Allam, the vestibular mucosa had the highest density of Langerhans cells (specialized dendritic cells) and a relatively low concentration of mast cells when compared with the bucca, palataum, lingua, sublingua, and gingiva. To the best of the knowledge of the present inventors, there are no immunotherapies designed to exploit the dendritic cell and mast cell distribution profile of the oral mucosa.

There remains a need in the art for noninvasive, oral allergic immunotherapies which retain the advantages of oral therapy but which reduce localized safety concerns and increase efficacy over the currently preferred sublingual delivery region.

Accordingly, the instant invention provides methods and articles for maximizing delivery of allergens to regions of the oral mucosa with a desirable relative dendritic to mast cell ratio. In particular, specific dosing and delivery methods of the invention target regions other than the sublingual mucosa, and certain embodiments specifically target the vestibular oral mucosa. The invention further provides methods and delivery embodiments designed to maximize the period of contact between the allergenic composition and the vestibular tissue or other targeted tissue. The dosing forms and delivery articles provided herein encourage relatively lengthy exposure times to regions of the oral mucosa having optimal dendritic/mast cell distribution profiles.

One embodiment of the invention provides a flexible porous pouch for insertion by a subject into an oral cavity of the subject and capable of fixedly conforming to a vestibular mucosal surface of the oral cavity. The pouch comprises a composition formulated for extended release and the composition comprises at least one allergen. In certain embodiments the pouch may be provided to the clinician or consumer as an empty flexible pouch suitable for receiving, containing and securing the composition.

According to a further embodiment of the invention, methods for decreasing sensitivity to one or more allergens and reducing symptoms of an allergy in a subject are provided. The methods comprise providing sustained exposure of one or more allergens associated with the allergy to an oral mucosal surface having a relatively high dendritic to mast cell ratio, and in specific methods the targeted oral mucosal surface is located substantially in a vestibular region of the oral cavity of the subject. In specific embodiments the allergenic active may be contained in a flexible pouch according to the invention, or in a dental hygiene product such as toothpaste, dental cream, mouthwash or mouth spray, gels, oral strips and the like. All these dosage forms have the advantage of exposing regions of the oral mucosa possessing a relatively high number of dendritic cells, in particular the vestibular oral mucosa, to allergenic actives for a sustained period of time. The methods avoid sustained contact with regions of the oral mucosa in close proximity to high concentrations of mast cells associated with emptying lymph nodes.

In some embodiments, the toothpaste, dental cream, mouthwash, or mouthspray composition induces development of immune tolerance while promoting oral health. The composition comprises a) toothpaste, dental cream, mouthwash or mouthspray base ingredients; and b) at least one allergen provided in natural form or as an extract of the allergen. Regimens suitable for optimizing the acquisition of immune tolerance to the allergen via this delivery form reflect ordinary use of the delivery form.

With respect to pouches, it is contemplated that allergenic active is released from the pouch by the action of saliva and that full disbursement of the active contents occurs across a prolonged period such as during sleep.

In another embodiment, personalized methods for decreasing a subject's allergic response to a specific environmental allergen are provided. The methods comprise identifying an allergen associated with the allergic response, mixing an extract of the identified allergen with an organic non-toxic filler material, filling a flexible porous pouch with the mixture, wherein the filled pouch is suitable for insertion by the subject into an oral cavity of the subject and capable of fixedly conforming to a vestibular mucosal surface of the oral cavity, and inserting the pouch so that it fixedly conforms to the vestibular mucosal surface.

Kits are also contemplated. In one embodiment the kit comprises a plurality of flexible porous pouches comprising a composition according to the invention and instructions comprising a dosing schedule effective for desensitizing the subject to the at least one allergen. Other kits provide a plurality of empty flexible porous pouches along with a set of vials containing extracts of common environmental allergens, an amount of organic non-toxic filler material; and instructions for mixing extract with the filler material and for filling the flexible porous pouch. These kits may be sold directly to consumers and may be packaged for particular allergic disorders, such as grass allergy, allergy to pets, dust mite allergy, and the like, or combinations thereof.

It is contemplated that kits may be designed on the basis of relevance to particular geographical areas, for example.

All references (e.g., printed publications such as books, papers, patents, patent applications, catalogs, databases) are incorporated herein by reference. In the event of a conflict or inconsistency, the present specification, as modified by any amendments thereto, shall control.

Although allergic sublingual immunotherapy (SLIT) has developed a good therapeutic and safety reputation during its relatively short availability as an alternative to subcutaneous immunotherapy (SCIT), it has recently been discovered that other regions of the oral mucosa may provide a superior immunogenic and safety profile.

In particular, researchers out of the University of Bonn recently conducted a comparative study of relevant cellular distribution across regions of the oral mucosa, including the bucca, gingiva, vestibula, lingua, and sublingua and reported that the vestibula had the highest density of Langerhans cells (specialized dendritic cells) and a relatively low level of mast cells. (Allam et al., SUMMARY, supra) Although the sublingual mucosa itself has few mast cells, they are located in the glands of that region and are considered responsible for the undesirable localized side effects of itching, lingering discoloration, and sublingual edema that are experienced by some subjects undergoing SLIT regimens requiring extended exposure of the allergen specifically to the sublingual tissue.

The present invention provides dosage and delivery forms designed to result in a distribution of allergen across the oral mucosal tissue that corresponds more favorably with the distribution profile of dendritic (Langerhans) cells and mast cells of the oral mucosa than dosage and delivery forms designed specifically for maximizing exposure to the sublingual mucosa typical in SLIT.

One embodiment of the invention is directed to flexible porous pouches. The pouches are suitable for insertion by a subject into an oral cavity of the subject and capable of fixedly conforming to a vestibular mucosal surface of the oral cavity, the pouch comprising a composition formulated for extended release, the composition comprising at least one allergen. (It will be appreciated that the pouch could optionally be inserted into the oral cavity of the subject by another individual.)

In some embodiments of any aspect of the invention, a composition is a nutraceutical composition. A nutraceutical composition may comprise one or more components typically found in a herbal or dietary supplement. In some embodiments, a nutraceutical composition comprises a vitamin, mineral, herb or other botanical other than tobacco (or a constituent, extract, or metabolite thereof), amino acid, fatty acid, or combination of any of these. In some embodiments, a nutraceutical composition comprises one or more components isolated from a foodstuff (e.g., a plant or animal substance suitable for consumption as food for nutritional purposes by, e.g., human subjects). Typically a foodstuff is a substance normally and ordinarily acquired for consumption and consumed by normal human subjects for nutritive and/or gustatory purposes (as distinguished, e.g., from substances that are not normally or ordinarily consumed but may be consumed under abnormal conditions such as famine or other situations in which access to customarily consumed foodstuffs is limited, etc.) In some embodiments of any aspect of the invention, a composition of the invention is or comprises a pharmaceutical composition in accordance with the laws and/or regulations of one or more countries or regions, e.g., a country or region in which the composition is provided to an end user, sold, and/or used. The pharmaceutical composition may be manufactured, tested, quality controlled, and/or labeled in accordance with such laws and/or regulations. In some embodiments, a pharmaceutical composition of the invention is sold without a prescription (over-the-counter). In some embodiments, a pharmaceutical composition is provided by prescription.

Flexible pouches suitable for containing the composition are known in the art, in particular in the context of chewing tobacco. Illustrative examples are disclosed in U.S. Application Serial No. 20100018540 "SMOKELESS TOBACCO PRODUCTS AND PROCESSES"; U.S. Application Serial No. 20070031539 "Personal caffeine delivery pouch"; U.S. Application Serial No. 20080152695, "ORAL/BUCCAL TRANSMUCOSAL DELIVERY METHODS FOR ELECTROLYTE COMPOSITIONS INCLUDING XYLITOL"; U.S. Application Serial No. 20080302682 "POUCH FOR TOBACCO OR TOBACCO SUBSTITUTE"; the entire disclosures of which are incorporated herein by this reference.

In some embodiments, the composition comprises, in addition to an allergen, one or more physiologically acceptable substance(s) that serve, e.g., as a filler material or matrix having the allergen contained therein or intermingled therewith. "Physiologically acceptable substance" includes substances (e.g., carriers, diluents, excipients) that do not produce an adverse or untoward reaction when administered to a mammalian subject, e.g., a human, in the amounts and at the locations used. Numerous such substances are discussed in Remington: The Science and Practice of Pharmacy by University of the Sciences in Philadelphia (editor), Lippincott Williams & Wilkins; $21^{St}$ ed. (2005), and earlier editions thereof, and other references known to those of ordinary skill in the art. In some aspects, a polymer matrix is physically associated with the allergen. For example, the allergen may be entrapped, embedded, or encapsulated by the polymer matrix. A matrix can be a macroscopic structure, which may comprise a semi-solid or viscous material, and/or may comprise a plurality of particles (nanoparticles, microparticles). A matrix may release the allergen by diffusion or as a result of breakdown or erosion of at least a portion of the matrix or filler material. In some embodiments, the filler material or matrix at least in part dissolves or disintegrates over time, thereby releasing the one or more allergens. In some embodiments, the filler material or matrix comprises a physiologically acceptable excipient that is susceptible to cleavage by salivary enzyme(s). In some embodiments, an excipient is a polymer. In some embodiments, the polymer is a non-protein polymer, e.g., a polysaccharide. In some embodiments, the excipient is a substance that is naturally present in one or more foods or is a generally recognized as safe (GRAS) substance as defined by the US Food and Drug Administration. In some embodiments, a filler material or matrix comprises soluble or insoluble plant fiber (e.g., from a plant that serves as a food) that resists digestive enzymes. Examples include non-starch polysaccharides such as arabinoxylans, cellulose, and various other plant components such as digestion-resistant dextrins, inulin, and oligosaccharides.

Extended release formulations are contemplated in order, for example, to ensure sufficient exposure to effectuate desensitization in a relatively short time frame. In some embodiments, by prolonging the duration of at least some exposures to the allergen, desensitization may occur within fewer days, weeks, or months following an initial use of the composition, than would otherwise be the case. Formulation techniques for achieving extended release in a salivary environment are known in the art. In some embodiments, an extended release formulation releases allergen over a period of at least 5 minutes, e.g., 5-15 minutes, 15-30 minutes, 30-60 minutes, 60-120 minutes, 2-4 hours, 4-8 hours, 8-12 hours, etc. In particular embodiments, the extended release formulation comprises a starch matrix incorporating the one or more allergens, said matrix being capable of dissolving in saliva thereby releasing the one or more allergens into the saliva. A person of ordinary skill in the art will be able to select formulation components which provide a desired extended leaching of the allergenic material across the exposure time frame.

The flexible porous pouch may be provided as a disposable single use pouch similar to pouches known for the containment of chewing tobacco products. After a subject's intended use, the pouch is thrown away. In certain embodiments, the pouch may be provided as an empty flexible porous pouch adapted for receiving, containing and securing a dose of a composition according to the invention. In other specific embodiments the flexible porous pouch may be fabricated from a material that dissolves in saliva. In these embodiments it is contemplated that a full dose is delivered by the point of complete dissolution.

In some embodiments, the contents of a flexible porous pouch of the invention include, in addition to an allergen, at least one breath freshening or flavoring ingredient. In some embodiments, use of the pouch may confer a feeling of breath freshness, well-being, and/or a pleasurable gustatory sensation. In certain embodiments, use of the inventive pouch may diminish a desire for food intake.

Allergens according to the invention may include any agent which triggers a measurable immune response. For example, an allergen may include any agent which triggers measurable production of IgE in at least some individuals exposed to the allergen (e.g., at least some atopic individuals). In many embodiments, an allergen comprises an agent that triggers an allergic reaction (type I hypersensitivity reaction) in at least some individuals exposed to the allergen (e.g., at least some atopic individuals). In some embodiments of the invention, the allergen is an air-borne allergen. Typically, the main route by which subject are exposed to such allergens is though inhalation. In some embodiments of the invention, the allergen is one to which subjects are mainly exposed by skin contact with the allergen. In some embodiments of the invention, the allergen is one to which subjects are mainly exposed by ingesting the allergen. In some embodiments of the invention, the allergen is one to which subjects are mainly exposed by injection Exemplary allergens according to the invention include allergens of plant, animal or fungal origin. Plant allergens include pollen, sap, leaves and plant toxins, while examples of fungal allergens include polypeptides produced by molds, *Aspergillus* and others. Animal allergens include polypeptides produced by insects, fecal allergens of dust mites and mammals, in particular of cats, and animal keratinacious dander. Specific examples include ragweed pollen, dust mite and dust mite excrement, animal dander and mold. Researchers have discovered that a combination of ragweed pollen and dust mite provides close to a "universal allergen" capable of affording desensitization to a wide variety of allergens. Other examples of allergens include food allergens, various insect venoms, and a number of industrial chemicals and pharmaceutical agents (e.g., penicillins, cephalosporins, cancer chemotherapy drugs, etc). Common sources of food allergens include peanuts, tree nuts, eggs, milk, shellfish (e.g., shrimp, crab), fish, wheat, soy and their derivatives.

One of ordinary skill in the art will appreciate that, in general, particular allergenic molecules (e.g., particular proteins) within allergens such as pollens, dusts, danders, molds, foods, etc, are responsible for triggering the allergic reaction. It is common to refer both to the particular allergenic molecules (e.g., particular proteins) and the materials in which they are found as "allergens", and that convention is use herein. Thus, reference to an "allergen" encompasses allergens in natural forms such as pollens, dusts, danders, molds, foods, or venoms, extracts of such natural forms of allergens, and allergenic molecules (e.g., particular proteins) that are at least partially purified or substantially purified or isolated from natural sources or produced using, e.g., recombinant DNA technology. The terms "protein" and "polypeptide" are used interchangeably herein. It will be appreciated that proteins can have modifications such as glycosylation, phosphorylation, acetylation, etc., and that a protein may be a single amino acid chain or can comprise multiple chains.

An allergen may be a modified form of a naturally occurring allergen. For example, an allergen can be chemically modified, e.g., to reduce its allergenicity. Such modified allergens may be referred to as an "allergoid". Allergoids may, for example, comprise allergens that have been treated with glutaraldehyde, formaldehyde or carbamylated. They may be polymerized or in monomeric form.

Many allergens contain multiple distinct allergenic proteins. Numerous specific allergenic proteins have been isolated from the natural allergen form in which they occur and/or cDNA encoding such protein(s) has been isolated and sequenced. Amino acid sequences of numerous protein allergens are available. Allergens may be designated as "major" and "minor" allergens. In some embodiments, a protein is considered a major allergen if the prevalence of IgE reactivity is >50% among individuals sensitive to the natural form of an allergen in which the protein occurs, with other allergens being considered "minor" allergens. In some embodiments, an allergen is a protein for which the prevalence of IgE reactivity is >5% among individuals sensitive to the natural form of an allergen in which the protein occurs. Protein allergens of animal, plant, or fungal origin are usually named using a systematic nomenclature developed by the World Health Organization and International Union of Immunological Societies (WHO/IUIS) Allergen Nomenclature Sub-committee under the auspices of the WHO and IUIS (see, e.g., Lockey, R F and Ledford, D K (eds.) "Allergens and Allergen Immunotherapy" 4th ed. 2008. Informa Healthcare, New York, incorporated by reference herein, e.g., Chapman M D. Allergen Nomenclature. Chapter 3 (pp. 47-58) therein. According to this nomenclature, the first three letters of the genus are followed by the first letter of the species and then a numeral. For example: Phl p 5 is a major allergen of *Phleum pretense* (timothy grass) pollen. The WHO/IUIS Allergen Nomenclature Sub-committee maintains an allergen database (WHO/IUIS Allergen Database) that contains numerous approved and officially recognized allergens. The database, which can be accessed on the website available at http://www.allergen.org, is searchable by allergen name and allergen source (common or scientific name). According to the WHO/IUIS nomenclature, isoallergens are defined as allergens from a single species, sharing similar molecular size, identical biological function, and greater than 67% amino acid sequence identity (Chapman M D, supra). It will be appreciated that multiple isoforms (variants that differ in amino acid sequence) of many allergens are found in nature. Isoallergens and isoforms are denoted by the addition of four numeral suffixes to the allergen name. The first two numerals distinguish between isoallergens and the last two between isoforms. Such two or four numeral suffixes will generally be omitted herein, but it should be understood that the various allergen isoallergens and isoforms known in the art are included within the scope of allergens of use in embodiments of the various aspects of the instant invention.

One of ordinary skill in the art will readily be able to obtain amino acid sequences for numerous protein allergens of plant, animal, or fungal origin, among others, as well as sequence of nucleic acids encoding such allergens, using publicly available information. For example, the WHO/IUIS Allergen Database provides UniProt accession number for numerous protein allergens and Genbank accession number for nucleic acids encoding them. SDAP (Structural Database of Allergenic Proteins) is a Web server (available at the University of Texas Medical Branch website available at http://fermi.utmb.edu/SDAP) that, among other things, allows the user to retrieve information for allergens (e.g., sequence information) from the most common protein sequence and structure databases (SwissProt, PIR, NCBI, PDB). The US National Center for Biotechnology Information (NCBI) databases (available at http://www.ncbi.nlm.nih.gov) such as GenBank provide information regarding amino acid sequences of numerous protein allergens and nucleic acids that encode them. UniProt accession numbers (acc. no.) for various allergens of interest are provided herein for illustrative purposes. The afore-mentioned databases are incorporated herein by reference, e.g., allergen names, accession numbers, and sequences, are incorporated herein by reference. One of ordinary skill in the art can readily identify sequences of other allergens. As noted above, one of ordinary skill in the art will appreciate that isoallergens and isoforms of many of these allergens exist. One of skill in the art will further appreciate that variations in one or more nucleotides of the nucleic acids encoding a particular protein may exist among individuals of a given species due to natural allelic variation. As a result of the degeneracy of the genetic code, many of these variations do not result in changes in amino acid sequence. One of ordinary skill in the art will further appreciate that an allergen protein may be synthesized as a precursor protein that contains one or more portions not found in the mature form. A mature allergen protein may have been processed intracellulary or extracellularly so as to remove one or more portion(s) of the preprotein. For example, a signal peptide may be removed, or a polypeptide chain may be cleaved to form two or more chains, optionally removing a portion of the precursor protein.

Plant pollens are major sources of airborne allergy throughout many areas of the world. In some embodiments of the invention, an allergen comprises grass pollen. Grasses, as used herein, include members of the family Poaceae (sometimes termed "true grasses"), rushes (Juncaceae) and sedges (Cyperaceae). Grasses are distributed widely throughout many regions of the world, with different species having variable importance in different geographical areas. For example, grass species common in at least some regions of Europe and/or the US include *Dactylis glomerata* (orchard grass), *Poa pratensis* (Kentucky bluegrass), *Lolium perenne* (ryegrass), *Anthoxantum odoratum* (sweet vernal), *Phleum pratense* (timothy), *Festuca eliator* (meadow fescue), *Agrostis alba* (redtop), and *Cynodon dactylon* (Bermuda grass). Grass allergens include, e.g., Poa a 1 (UniProt acc. no. Q9ZP03) and Poa p 5 (UniProt acc. no. Q9FPR0). In some embodiments of the invention, an allergen is from a grass within the *Dactylis, Poa, Lolium, Anthoxantum, Phleum, Festuca, Agrostis,* or *Cynodon* genus, e.g., any of the aforementioned species. For example, an allergen can comprise a Poa a, Poa p, or Phl p protein.

In some embodiments of the invention, an allergen is pollen (or an extract or component thereof) of a tree or shrub that is a member of the Cupressaceae family. It should be noted that the Cupressaceae (cypress) family includes a number of species whose common name includes the word "cedar". In some embodiments, the allergen is pollen from a species in the subfamily Cupressoideae, e.g., a member of the genus *Chamaecyparis* or *Juniperus* ("juniper"). In some embodiments, the allergen is pollen from *Cryptomeria japonica* (family Cupressaceae, subfamily Taxodioidea), commonly referred to as Sugi or Japanese cedar. Japanese cedar pollen is the major cause of pollinosis in Japan. Approximately 15% of the Japanese population was affected by Japanese cedar pollinosis in 2002 (Okuda M., Ann Allergy Asthma Immunol, 91: 288-96, 2003), and the prevalence has reportedly increased to an estimated 26.5% in 2008 (see Okubo, K., Allergol Int., 57(3):265-75 2008, incorporated by reference). Many patients with cedar pollinosis have also been sensitized to *Chamaecyparis obtusa* pollen (Japanese cypress, hinoki cypress or hinoki), which disperses after Japanese cedar pollen. In these individuals, symptoms of Japenese cedar pollinosis are frequently followed by those of cypress pollinosis, often resulting in a symptomatic period lasting for about 4 months (e.g., from February to May). In some embodiments, the invention provides compositions and methods of use in desensitizing individuals who suffer from Japanese cedar and/or Japanese cypress pollinosis. Cry j 1 (UniProt acc. no. P18632) and Cry j 2 (UniProt acc. no. P43212) are major allergens of *Cryptomeria japonica* pollen. See, e.g., Yasueda H, et al., J Allergy Clin Immunol., 71(1 Pt 1):77-86, 1983; Sakaguchi M, et al. Allergy, 45:309-312, 1990, for discussion. cDNAs encoding these allergen proteins have been cloned and sequenced. See, e.g., Sone T, et al., Biochem Biophys Res Commun. 199:619-625, 1994; Komiyama N, et al. Biochem Biophys Res Commun. 201:1021-1028, 1994; Namba M, et al., FEBS Lett. 353:124-128, 1994; and PCT/US1992/005661 (WO1993001213—ALLERGENIC PROTEINS AND PEPTIDES FROM JAPANESE CEDAR POLLEN). Cry j 3 has been identified, and sequences are available (see, e.g., Futamura N, et al. Biosci Biotechnol Biochem. 66(11):2495-500, 2002; Futamura N, et al. Tree Physiol. 26:51-62, 2006). Other allergens, e.g., Cry j 4, Cry j 5, Cry j 6 have been identified as well (Matsumura D, et al., Biol Pharm Bull. 29(6):1162-6; 2006). In some embodiments, an allergen comprises a Cry j protein, e.g., Cry j 1, Cry j 2, Cry j 3, Cry j 4, Cry j 5, Cry j 6.

Cha o 1 (UniProt acc. no. Q96385) and Cha o 2 (UniProt acc. no. Q7M1E7) are major allergens of Japanese cypress, cDNAs for which have been cloned and sequenced (Suzuki M, et al., Mol Immunol. 33(4-5):451-60, 1996; Mori T, et al, Biochem Biophys Res Commun. 263(1):166-71, 1999). In some embodiments an allergen comprises a Cha o protein, e.g., Cha o 1, Cha o 2.

Ashe juniper (*Juniperus ashei*, family Cupressaceae, sometimes called mountain cedar) and Arizona cypress (*Cupressus arizonica*, family Cupressaceae) pollens cause seasonal allergic rhinitis in certain parts of the US and Northern Mexico while Italian cypresses (*Cupressus semperverins*, family Cupressaceae) cause pollinosis in the Mediterranean region (e.g., France, Italy, Israel). In some embodiments, the invention provides compositions and methods of use in desensitizing individuals who suffer from allergy to one or more such pollens. Jun a 1 and Jun a 2 are major allegens of juniper pollen. See, e.g., Midoro-Horiuti T, J Allergy Clin Immunol. 104(3 Pt 1):608-12, 1999; Midoro-Horiuti T, J Allergy Clin Immunol. 104(3 Pt 1):613-7, 1999; Yokoyama M, Biochem Biophys Res Commun. 275(1):195-202, 2000). The amino acid sequence of Jun a 1 (UniProt acc. no. P81294) shows significant identity with those of Cry j 1 and Cha o 1, respectively. The amino acid sequence of Jun a 2 (UniProt acc. no. Q9FY19) shows about 70% and 82% identity with those of Cry j 2 and Cha o 2, respectively. In some embodiments an allergen comprises a Jun a protein, e.g., Jun a 1, Jun a 2.

The Betulaceae, or birch family, includes six genera of deciduous nut-bearing trees and shrubs, including the birches (genus *Betula*), alders (genus *Alnus*), hazels (genus *Corylus*), hornbeams and hop-hornbeams. In some embodiments of the invention, the allergen comprises pollen (or an extract or component thereof) of a member of the birch family. In some embodiments the pollen is from a member of the subfamily Betuloideae. In some embodiments, the pollen is from genus *Betula*, e.g., *Betula verrucosa*. Birch pollen allergens include, e.g., Bet v 1, Bet v 2, Bet v 3, Bet v 4, Bet v 5, Bet v 6, and Bet v 7. In some embodiments, the pollen is from genus *Alnus*, e.g., *Alnus glutinosa*. Alder pollen allergens include, e.g., Aln g 1 and Aln g 4. In some embodiments, the pollen is from genus *Corylus*, e.g., *Corylus avellana*. In some embodiments, an allergen comprises a Bet v protein.

Various other plants that are significant causes of allergy belong to the families Asteraceae, Amaranthaceae, Urticaceae, Euphorbiaceae, and Plantaginaceae. In some embodiments of the invention, a composition comprises a pollen (or an extract or component thereof) from a plant of the Asteraceae, Amaranthaceae, Urticaceae, Euphorbiaceae, or Plantaginaceae family. Examples of such plants include ragweed, cocklebur, marsh elder, mugwort, feverfew, pellitory, goosefoot, plantain, and Russian thistle. Ragweeds (*Ambrosia* species), for example, are a genus of flowering plants from the sunflower family (Asteraceae) and represent a highly significant cause of allergy in North America that is becoming increasingly important in Europe. Four major families of proteins may represent the major cause of allergic reactions to pollens of such plants: the ragweed Amb a 1 family of pectate lyases (e.g., UniProt accession numbers P27759, P27760, P27761, P27762 from *Ambrosia artemisiifolia* (short ragweed)); the defensin-like Art v 1 family (e.g., from mugwort and feverfew, e.g., UniProt acc. no. Q84ZX5 from *Artemisia vulgaris* (mugwort)); the Ole e 1-like allergens, Pla l 1 from plantain, and Che a 1 from goosefoot, and the nonspecific lipid transfer proteins Par j 1 and Par j 2 from pellitory (Gadermaier G, et al. Curr Allergy Asthma Rep. 4(5):391-400, 2004)). Amb a 1 was among the first of these allergens for which cDNA was cloned and sequenced. See, e.g., PCT/US1990/001310 (WO/1990/011293—ALLERGENIC PROTEINS FROM RAGWEED AND USES THEREFOR). In some embodiments of the invention, an allergen comprises an Amb a, Art v, Ole e-like, Pla 1, Par j protein, or combination thereof. Mixtures of pollens from such plants (and extracts and components thereof) are contemplated. Plant allergens of natural rubber latex derived from a variety of different plant species (e.g., *Hevea*, such as *Hevea brasiliensis*) are contemplated.

Dust mites are significant sources of allergy in many areas of the world. Allergens are found in dust mite feces and the mite body. Dust mite species of significant importance include, for example, *Dermatophagoides farinae, D. pteronyssinus*, and *Tyrophagus putrescentiae*. House dust mite allergens include, for example, Der p 1 (UniProt acc. no. P08176), Der p 2 (UniProt acc. no. P49278), Der p 3 (UniProt acc. no. P39675), and Der p 4 from *D. pteronyssinus* and Der f 1 (UniProt acc. no. P16311), Der f 2 (UniProt acc. no. Q00855), and Der f 3 (UniProt acc. no. P49275) from *D. farinae*. In some embodiments of the invention an allergen comprises a Def p, Der f, or Tyr p protein.

Animal allergens occur, for example, in dander, feathers, hair, saliva, and excretions (e.g., urine). Domesticated animals such as cats (*Felis domesticus*) and dogs (*Canis lupus familiaris*) are common sources of allergy. Fel d 1 (UniProt acc. no. P30438 (chain 1); UniProt acc. no. P30440 (chain 2)), Fel d 3, and Fel d 4 are major cat allergens. Can f 1 (UniProt acc. no. 018873) and Can f 2 (UniProt acc. no. 018874) are major dog allergens. In some embodiments an allergen comprises a Can f or Fel d allergen. Rodents such as mice (e.g., *Mus musculus*), rats (e.g., *Rattus norvegicus*), and rabbits (e.g., European rabbit (*Oryctolagus cuniculus*)) are common sources of allergy. Identified allergens include, e.g., *Mus* m 1, Rat n 1, and Ory c 1, in these species, respectively. Individuals may, for example, encounter such animals as pets, as pests, or in an occupational context (e.g., as laboratory animals). In some embodiments an allergen comprises a *Mus* m, Rat n, or Ory c protein. Farm animals such as horses, cows, sheep, goats are also causes of allergy, and in some embodiments an allergen from such animal is present in an inventive composition.

Insects and insect venoms are notable sources of allergens. Cockroach allergens are significant causes of allergy in many areas of the world. Cockroach species include, for example, *Blattella germanica* (German cockroach) and *Periplaneta americana* (American cockroach), and *Blatta orientalis* (Oriental cockroach) Cockroach allergens include, for example, Bla g 1, Bla g 2, Bla g 5, Bla g 5, Bla g 6, Bla g 7, and Bla g 8 (from *B. germanica*) and Per a 1, Per a 3, Per a 6, Per a 7, Per a 9, and Per a 10 (from *P. Americana*). In some embodiments an allergen comprises a Bla g, Per a, or Bla o allergen. Ant, moths, fleas, flies (e.g., house fly, horse fly, mayfly), and mosquitos are also sources of allergens. In some embodiments an allergen is a cockroach, ant, moth, flea, fly, or mosquito protein.

Insect venoms, (e.g., from insects of the order Hymenoptera, e.g., bees, hornets, or wasps) that are potential causes of severe allergic reactions include venoms from European Hornet (*Vespa crabro*), Honey Bee (*Apis mellifera*), Hornet (*Dolichovespula* spp.), Paper Wasp (*Polistes* spp.), Yellow Jacket (*Vespula* spp.), White (Bald)-Faced Hornet (*Dolichovespula* maculata), Yellow Hornet (*Dolichovespula* arenaria). In some embodiments an allergen is a venom (or extract or component thereof) of a bee, wasp, or hornet. For example, an allergen can comprise an Api, Dol, or Ves protein.

Fungi (e.g., fungal spores or fragments (e.g., hyphal fragments)) are significant sources of allergy. *Alternaria* (e.g., *Alternaria alternata* (*Alternaria* rot fungus)), *Cladosporium* (e.g., *Cladosporium herbarum, Cladosporium cladosporioides*), *Aspergillus* (e.g., *Aspergillus fumigatus, Aspergillus niger*), *Fusarium, Penicillium* are exemplary allergenic fungi of interest. In some embodiments, an allergen comprises a protein found in or produced by *Alternaria, Cladosporium, Aspergillus, Fusarium, Penicillium*, or other fungus. For example, an allergen can comprise an Alt a, Asp a, Asp n, Cla or Pen protein.

Methods of obtaining allergens are well known in the art. For example, pollens can be collected from the respective plants, which may be cultivated or in the wild. Fungal extracts can be produced from pure culture mycelial mats or allergens can be isolated from culture medium. Rusts and smuts can be obtained from natural growths. Epithelial extracts can be produced from the hide, hair, or feathers containing the natural dander, or from separated dander. Insect and mite extracts can be produced from the whole body of the insects or mite, respectively. In the case of insect venoms, venom or venom-containing organs can be isolated or a whole body extract can be used. House dust can be made from various dusts ordinarily found in the home (e.g., upholstery dust, mattress dust, or general dust accumulating on surfaces). Other dusts (e.g., grain dust, wood dust, cotton dust) can be collected from the appropriate location. Food extracts can be prepared from the edible portions of the respective foods, e.g., freshly obtained foods.

Methods suitable for allergen processing, e.g., production of allergen extracts, purification of allergen molecules, etc., are well known in the art. Very briefly, source allergen material (e.g., pollen, insect, dander) can be subjected initially to pulverization, drying, defatting (by extraction using organic solvent), or other steps as appropriate for the particular allergen. Centrifugation can be used, e.g., to separate solid or particulate matter. Resulting material can be incubated in an aqueous medium (e.g., water or suitable buffered solution, e.g., ammonium bicarbonate, phosphate buffered saline, etc.) for a suitable period of time to at least partly solubilize proteins. Crude extract can be processed using, e.g., dialysis, filtration, fractionation, chromatography, etc. In some embodiments, one or more steps is performed to at least partly remove low molecular weight components, concentrate the extract, etc. Extracts can be sterilized, e.g., using filtration and/or irradiation. Other processing steps can be applied as known in the art. Numerous specific protocols are available.

Extracts of allergens specifically processed for safe use in human immunotherapy are available commercially. For example, GREER Laboratories Inc. Allergy and Immunotherapy division publishes a brochure entitled "Human Allergy Products and Services" available on-line at the company website currently at http://www.greerlabs.com/files/catalogs/HumanAllergyCatalog.pdf. GREER also publishes a brochure entitled "Source Materials Products and Services" available online at the company website currently at http://www.greerlabs.com/files/catalogs/SourceMaterials Catalog.pdf, which details available allergens that can be used as raw materials for production of allergen extracts or more highly purified allergen protein preparations. Both publications are incorporated herein by reference. Other commercial suppliers of allergens and/or allergen extracts include ALK Abello, Inc., Allermed Labs, and HollisterStier. An extensive list of allergen extracts is found in Remington, supra. Allergen extracts typically contain multiple proteins, e.g., multiple allergenic proteins, present in the natural form of the allergen. Extracts can be prepared from, e.g., pollens (e.g., of trees, shrubs, grasses, other plants such as those often termed "weeds"), animal epithelia, feathers, fungal mycelia or spores, smuts, mites, insects, insect venoms, foods, dusts, etc. In some embodiments, an extract is prepared essentially from a single natural allergen (e.g., obtained from a single species of plant, animal, insect, fungus, etc.). Mixtures are contemplated. In some embodiments an extract is derived from multiple different plant pollens (e.g., weed mixture, tree mixture, grass mixture), multiple different fungi or smuts, multiple different insect venoms, multiple different animal epithelia, etc. Fungal extracts can be prepared from mycelia and/or spores (e.g., *Alternaria, Cladosporium*) and/or from culture filtrate material (e.g., *Aspergillus*). In some embodiments, one or more allergen protein(s) is further purified, e.g., from an extract comprising multiple proteins. One of ordinary skill in the art will readily be able to purify allergen protein(s) of interest using methods known in the art for protein purification. See, e.g., Cutler, P. (ed.) *Protein Purification Protocols, Methods in Molecular Biology*, Volume 244, 2004; Simpson, R J., et al., *Basic Methods in Protein Purification and Analysis: A Laboratory Manual* Cold Spring Harbor Laboratory Press, 2008; Richard R Burgess and Murray P. Deutscher (eds.) Methods in Enzymology: *Guide to Protein Purification, 2$^{nd}$* ed., Academic Press, 2009. Purification can entail chromatographic methods (e.g., based on size, hydrophobicity, affinity, etc.), immunological methods, electrophoretic methods, etc. Specific protocols for preparing various at least partially purified allergen proteins are available. In some embodiments, an extract or at least partially purified protein preparation comprises at least 70%, 80%, 90%, 95% or more protein by weight. In some embodiments, a protein is considered pure when it is removed from substantially all other compounds or entities other than a solvent and any ions contained in the solvent, e.g., the protein constitutes at least about 90%, e.g., at least 91%, 92%, 93%, 94%, 95%, 96%, 97%, 98%, 99%, or greater than 99% of the dry weight of the composition or on a weight per volume basis (excluding the solvent and ions). In some embodiments, a particular allergen protein of interest is considered pure if it constitutes at least about 90%, e.g., at least 91%, 92%, 93%, 94%, 95%, 96%, 97%, 98%, 99%, or greater than 99% of the protein content in the protein preparation by dry weight. Methods for assessing purity are known in the art and include, e.g., chromatographic methods, immunological methods, electrophoretic methods, mass spectrometry, etc. Any of the polypeptides described herein may be purified, in various embodiments. An extract or purified protein preparation can be provided in various formats. For example, an extract or purified protein preparation dried, e.g., lyophilized, or provided in aqueous medium, optionally comprising a protein stabilizing agent such as glycerin, a preservative, etc.

Mixtures of individual allergen proteins are contemplated. Allergen protein mixtures can comprise allergen proteins from the same species or from multiple different species, which may be in the same or different genera, subfamily, family, etc. In some embodiments, an allergen protein encoded by a gene homologous to that which encodes a particular allergen protein of interest can be used. For example, orthologous genes, i.e., genes in different species that are similar to each other because they originated by vertical descent from a single gene of the last common ancestor, can be used.

Also contemplated as within the scope of the invention are nutraceutical food additives, for example plant extracts, with demonstrated immunosuppresive character and/or confirmed efficacy in diminishing allergic response.

In some embodiments, an allergen comprises a recombinantly produced protein. Methods for producing proteins using recombinant DNA technology are well known in the art and are described in standard references such as Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., editions as of 2008; Sambrook, Russell, and Sambrook, *Molecular Cloning: A Laboratory Manual*, 3$^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Burns, R., *Immunochemical Protocols* (Methods in Molecular Biology) Humana Press; 3rd ed., 2005, all of which are incorporated herein by reference. Any suitable vectors, e.g., plasmids, viruses (e.g., DNA or RNA viruses), cosmids, etc., can be used to introduce a nucleic acid that encodes an allergen protein into a host cell, in various embodiments. One of ordinary skill in the art would appreciate that due to the degeneracy of the genetic code, any of a wide variety of nucleic acid sequences can encode a protein of interest (e.g., an allergen) and can accordingly be used in various embodiments of the invention relating to recombinant production of allergens. In some embodiments, a nucleic acid sequence is codon optimized for production of the protein in a host cell of interest. Any suitable expression system can be used. Various host cells, e.g., bacterial, fungal, insect, vertebrate (e.g., mammal), can be used in various embodiments. In some embodiments a host cell is selected based at least in part on the allergen. For example, in some embodiments a plant allergen can be produced in plant cells; a vertebrate allergen can be produced in vertebrate cells; a fungal allergen can be produced in fungal cells. An allergen could be produced using a transgenic approach, e.g., a transgenic plant. In some embodiments, the sequence of a recombinantly produced allergen comprises a fragment or variant of the sequence of a naturally occurring allergen protein. For example, a fragment may be a continuous sequence consisting of at least 20%, 30%, 40%, 50%, 60%, 70%, 80%, 90%, or more of the full length naturally occurring allergen protein. A variant has one or more amino acid substitutions, deletions, or additions (e.g., insertions) as compared with a naturally occurring allergen protein. For example, a variant may comprise a sequence at least 70%, 80%, 90%, 95%, 96%, 97%, 98%, 99%, or more identical to a naturally occurring allergen protein over a window of at least 50%, 60%, 70%, 80%, 90%, 95%, 96%, 97%, 98%, 99%, or more of the naturally occurring antigen, allowing the introduction of gaps to maximize identity. Percent identity can be calculated with the use of a variety of computer programs known in the art. For example, computer programs such as BLAST2, BLASTN, BLASTP, Gapped BLAST, etc., generate alignments and provide percent identity between a sequence of interest and sequences in any of a variety of public databases. The algorithm of Karlin and Altschul (Karlin and Altschul, Proc. Natl. Acad. Sci. USA 87:22264-2268, 1990) modified as in Karlin and Altschul, Proc. Natl. Acad. Sci. USA 90:5873-5877, 1993 is incorporated into the NBLAST and XBLAST programs of Altschul et al. (Altschul, et al., J. Mol. Biol. 215:403-410, 1990). To obtain gapped alignments for comparison purposes, Gapped BLAST is utilized as described in Altschul et al. (Altschul, et al. Nucleic Acids Res. 25: 3389-3402, 1997). When utilizing BLAST and Gapped BLAST programs, the default parameters of the respective programs are used. A PAM250 or BLOSUM62 matrix may be used. See the Web site having URL www.ncbi.nlm.nih.gov for these programs. In a specific embodiment, percent identity is calculated using BLAST2 with default parameters. In some embodiments, a variant has up to about 1%, 5%, 10%, 20%, or 30% amino acid substitutions, insertions, or deletions. In some embodiments, a variant has between 1 and 10 amino acid substitutions, insertions, or deletions.

In some embodiments, an allergen may be a fusion protein comprising at least a portion of an allergen protein comprising at least one allergenic epitope and a heterologous polypeptide. In some embodiments, the fusion protein comprises a tag, e.g., an epitope tag, of use in purifying the protein. In some embodiments, an allergen, e.g., a fusion protein, is expressed in a plant, e.g., in leaves or seeds. Such leaves or seeds can be used to prepare a composition of this invention. For example, a nucleic acid encoding the allergen can be expressed under control of an appropriate promoter to achieve expression in the plant or a portion thereof. A plant can be a transgenic plant or the protein can be transiently expressed, e.g., using a viral vector. In some embodiments a fusion protein comprises an allergenic epitope (e.g., an epitope of Japanese cedar pollen or other allergenic pollen) fused with at least a portion of a seed storage protein such as glycinin. A fusion protein could comprise multiple different allergen proteins or portions thereof. Methods such as solid phase peptide synthesis or protein ligation could be used to synthesize polypeptides in some embodiments, particularly if relatively short.

In some embodiments, a polypeptide that comprises one or more epitope(s), e.g., epitope(s) recognized by human T-cells derived from a naturally occurring allergen is used as an allergen in the instant invention. In some embodiments, the polypeptide comprises human T-cell epitope(s) derived from at least two different allergens, e.g., 2, 3, 4, 5, 6, or more different allergens. In some embodiments, the total number of T-cell epitopes is between 2 and 10. The epitopes may be separated from each other by 1 or more amino acids that serve as a spacer. A spacer can be, e.g., 1, 2, 3, 4, or 5 amino acids long, up to about 25 amino acids. In general, any amino acids can be used as spacers. In some non-limiting embodiments, relatively small amino acids such as Gly, Ala, Ser are used, but other amino acids could be used. For example, Cry-consensus peptide is a polypeptide containing six major human T-cell epitopes derived from both Cry j 1 and Cry j 2 (Tsunematsu M, et al. Allergology International. 56(4):465-72, 2007). Its sequence is: MKVTVAFNQFGPN-RR-VFIKRVSNVIIHG-RR-IDIFASKNFHLQKNTIGTG-RR-WKNNRIWLQFAKLTGFTLMG-RR-LKMPMYIAGYKTFDG-RR-VDGIIAAYQNPASWK (SEQ ID NO: 1). The T-cell epitopes are underlined. Epitopes 1, 2, and 5 (starting from the left) are Cry j 1 epitopes. Epitopes 3, 4, and 6 are Cry j 2 epitopes. T cell epitopes of a variety of allergens have been identified and could be used in embodiments of the invention. An epitope can be a linear epitope or a conformational epitope.

According to specific embodiments, the composition, comprises allergens selected from the group consisting of pollen, dust mite, mold and animal dander. Personalized regimens are contemplated wherein the subject or the subject's medical advisor selects allergens based on specific clinical symptoms wherein the allergen is relevant to the subject's environment, such as specific pet dander, geographically circumscribed pollens, or barnyard dander and the like. In personalized methods the subject exhibits clinical symptoms of an allergy and the one or more allergens are selected based on association with the allergy. In very specific embodiments based on a "universal" allergen approach, the allergen consists of ragweed pollen and dust mite, although the composition may comprise other allergens as well. In some embodiments, an allergen consists of a pollen allergen and an insect allergen. In some embodiments, an allergen consists of a pollen allergen and a mite allergen.

In some embodiments, an allergen extract is provided in a liquid form. For example, an allergen extract can be provided in water, glycerin, or a combination thereof. In some embodiments, an allergen extract is provided in substantially dry form, e.g., as a powder, e.g., in lyophilized form. In some embodiments, an allergen is provided in tablet form, wherein the tablet is inside the pouch, and the pouch optionally further contains one or more substances that serve as a filler material. In at least some of these embodiments, an allergen-containing tablet such as those used in SLIT (or contents thereof) can be employed. The tablet can contain allergen extract in lyophilized form. In some embodiments the tablet is a rapidly disintegrating tablet. In some embodiments, a five-grass pollen SLIT tablet (Stallergènes S A, France) can be used. The extracts are from pollen of perennial rye grass (*Lolium perenne*), meadow grass (*Poa pratensis*), timothy grass (*Phleum pratense*), cocksfoot (*Dactylis glomerata*) and sweet vernal grass (*Anthoxanthum odoratum*) and are sold under the name Oralair®. In some embodiments, a Grasax® tablet is used (ALK Grass tablet, ALK-Abelló A/S, Hørsholm, Denmark). The active substance in Grasax is a standardised allergen extract of grass pollen from timothy (*Phleum pratense*). Other ingredients in Grasax are gelatine (fish source), mannitol, and sodium hydroxide. Of course other excipients could be used as known in the art of tablet formulation. The tablet can be provided within a flexible porous pouch, optionally together with a filler material. The tablet may be at least in part surrounded by the filler material. In some embodiments, the allergen diffuses through the filler material to reach the vestibular, buccal, and/or gingival mucosa. The filler material may provide for an increased contact area of the allergen with the oral mucosa as compared with the area of the tablet.

One of ordinary skill in the art will appreciate that the amount of allergen(s) used in a composition of the invention (e.g., composition for inclusion in a flexible porous pouch or a dental hygiene composition (as discussed below)) can vary based on a number of factors such as, for example, the particular allergen(s) and the potency of the allergen preparation used. Allergens can be detected and/or quantified using methods known in the art, and such methods can be used to characterize allergen preparations (e.g., allergen extracts), e.g., with respect to allergen content and/or potency. For example, immunological methods such as immunoblotting or ELISA assays using, e.g., an appropriate monoclonal antibody, or other types of binding assays for detecting and/or quantifying proteins known in the art are applicable to many allergens of interest herein. Mass spectrometry could be used. In vivo or in vitro bioassays may be used to quantify biological activity. For example, skin prick tests can be performed on individuals known to be allergic to a particular allergen, and one or more indicators of allergic response (e.g., wheal area) or allergen-specific IgE production, can be measured. Skin prick tests can be standardized, e.g., using a specific delivery device, technique, and specified amount of allergen preparation. In vitro bioassays include measuring mediator release (e.g., histamine, cytokines, or lipid mediators) from appropriate cells, e.g., sensitized cells. An in-house reference standard can be produced (e.g., based on in vivo bioassays) and in vitro tests can be used to compare the potency of subsequent batches of allergen with the in-house reference and potency can be assigned as arbitrary units. A variety of units are in use to quantify allergen content and/or potency of allergen preparations. See, e.g., Remington, supra, and Lockey, R F and Ledford, D K, supra. For example, allergen content of allergen preparations can be expressed as weight-to-volume or Protein Nitrogen Units. In the US, standardized extracts are typically labeled as Allergy Units (AU)/ml or Bioequivalent Allergy Units (BAU)/ml. BAU is a standard established by the FDA, which provides a variety of different reference extracts that can be used to establish potency. In Japan, allergen content of allergen preparations is often expressed using Japanese Allergy Units (JAU) measured by ELISA. In Europe, a number of country-specific or company-specific standards are in use. For example, in-house reference standards can be established and used to quantify the strength of subsequently produced batches of allergen preparation. For example, an in-house reference index-of-reactivity (IR) can be used, wherein, for example, 100 IR/ml is defined as the concentration eliciting, by means of skin prick testing, a geometric mean wheal size of 7 mm in diameter in 30 patients sensitive to the corresponding allergen. If desired, any one or more of such approaches can be employed with regard to the allergen preparations of use in the instant invention.

In some embodiments, a composition of the invention (e.g., a composition for inclusion in a flexible porous pouch or a dental hygiene product or chewing gum) can be formulated so that a typical use provides between 1 pg to 15 mg of one or more allergen proteins(s), e.g., between 1 ng and 1.5 mg of one or more allergen protein(s), e.g., between 100 ng and 100 µg of one or more allergen protein(s). In some embodiments, a composition of the invention (e.g., a composition for inclusion in a flexible porous pouch or a dental hygiene product or chewing gum) can be formulated so that typical use provides (e.g., on a daily basis or over a period of time such as a week) between 0.01 and 100 times an amount of allergen useful in a SLIT regimen, e.g., between 0.1 and 10 times, or between 0.5 and 2 times an amount useful in a SLIT regimen. For example, in some embodiments, a composition (e.g., dental hygiene product) comprising Cry j 1 and/or Cry j 2 can provide between 20 JAU and 20,000 JAU on a weekly basis, e.g., between 200 JAU and 2000 JAU. In some embodiments, a composition contains 1, 2, 3, 4, 5, or more allergen protein(s), wherein each allergen protein may independently be present in any of the afore-mentioned quantities and/or the total amount of allergen present may be any of the afore-mentioned quantities. One of skill in the art would readily select an effective amount for inclusion in a composition or product of the invention. Homeopathic amounts of allergen are also contemplated for use in inventive compositions (e.g., dental hygiene product). For example, a 30c homeopathic dilution of an allergen extract or other allergen preparation can be used. As known in the art, a 30c dilution represents 30 sequential 1 in 99 dilutions of the stock solution. In some embodiments, a 15c to 60c dilution is used. In some embodiments, the resulting solution theoretically contains no molecules of allergen or of the original solution.

Methods for decreasing sensitivity to one or more allergens and reducing symptoms of allergy in a subject are also provided. The method comprises providing sustained exposure to one or more allergens associated with the allergy on an oral mucosal surface located substantially in a vestibular region of the oral cavity of the subject. In certain embodiments the sustained exposure is provided by insertion of a flexible porous pouch capable of fixedly conforming to a vestibular mucosal surface of the oral cavity wherein the pouch contains a composition according to the present invention, e.g., the nutraceutical composition or pharmaceutical composition according to the invention. It will be appreciated that the buccal and/or gingival mucosa may also be exposed to allergen through use of inventive delivery forms. Further provided are flexible porous pouches capable of conforming to the buccal mucosa wherein the pouch contains a composition according to the present invention.

In some aspects, methods of treating a subject suffering from or at risk of an allergic condition (e.g., allergy to one or more allergens disclosed herein) are provided, wherein a method comprises prescribing, recommending, or suggesting use of an inventive composition or product to the subject. Optionally the method comprises determining that the subject is allergic to an allergen, e.g., based on history and/or one or more diagnostic tests. In some aspects, methods of treating a subject suffering from or at risk of an allergic condition are provided (e.g., self-treatment methods), wherein a method comprises use of an inventive composition or product by the subject. A subject or may be aware of particular allergens that trigger an allergic reaction and selects a particular composition or product based on such awareness.

In other specific embodiments sustained exposure is provided by ordinary use of a dental hygiene product such as toothpaste, dental cream, mouthwash or mouthspray. The invention provides suitable toothpaste, dental cream, mouthspray and mouthwash composition embodiments comprising base ingredients of the dental hygiene product and further comprising one or more allergens. The one or more allergens may be provided in suitably ground or refined natural form, or as processed into an extract of the allergen or otherwise at least partially purified or isolated (e.g., separated from one or more substances with which it naturally occurs or produced by man (e.g., using recombinant DNA technology)). The former specific embodiment contemplates that the natural form is non-toxic and safe for inadvertent consumption. Allergen extracts processed specifically for safety and efficacy in all forms of AIT are well known in the art and available from commercial vendors such as GREER Laboratories (see, supra). Certain proprietary allergen blends specifically intended for nutraceutical compositions are particularly suited to these embodiments. As a non-limiting illustrative example, proprietary plant blends intended as nutraceutical food additives are known, including Pantescal® available from Bionap, Italy, which have demonstrated immunosuppressive efficacy in individuals with certain grass allergies, and are suitable for inclusion in this and other embodiments of the instant invention.

Base formulations for dental hygiene products are well known to a person of skill in the art. One illustrative example of a base toothpaste composition includes ingredients which comprise a combination of known amounts of: vegetable glycerin; sorbitol; hydrated silica; purified water; xylitol; carrageenan; sodium lauryl sulfate; titanium dioxide; propylparaben; methylparaben; sodium benzoate; and a flavoring agent. One of ordinary skill in the art will appreciate that toothpaste can encompass a paste, gel, or combination thereof. One of ordinary skill in the art will also appreciate that a variety of ingredients may be included in an inventive toothpaste to serve, for example, as thickening/gelling agents, humectants, surfactants, flavoring or sweetening agents, polishing agents, etc. For example, thickening agents include various cellulose derivatives (e.g., cellulose ethers such as carboxymethyl cellulose), starch, gum (e.g., gum tragacanth, xanthan gum), carrageenan, and silica-based thickening agents. Humectants include, e.g., glycerin, glycols (e.g., propylene glycol, polypropylene glycol, polyethylene glycol). A surfactant (which may or may not be present) may be anionic, nonionic, amphoteric, zwitterionic, cationic, or mixtures thereof. Exemplary anionic surfactants include, for example, water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Exemplary nonionic surfactants include triblock copolymers composed of polyoxypropylene and polyoxyethylene, for example, poloxamers (sold under the trade name Pluronics, for example). Sweetening agents include, e.g., saccharin, xylitol, sorbitol, aspartame. Polishing agents include a variety of different abrasive materials and may be silica-based or non-silica based (e.g., calcium or aluminum-based, e.g., calcium carbonate, alumina, aluminum hydroxide). Flavoring agents include a variety of plant-derived oils, for example. In some embodiments, water, thickening/gelling agent, polishing agent, humectant, surfactant together amount to between 70% and 99.99% by weight of the composition. In some embodiments, water, thickening/gelling agent, polishing agent, humectant, and/or surfactant is present at between 5% and 70% by weight, with the total of these ingredients together amounting to between 70% and at least 99.99% by weight of the composition. In some embodiments, a polishing agent is present in an amount between 5% and 50% by weight, based on the total weight of the composition. In some embodiments, a surfactant is present in amount between 0.5% and 15% by weight, e.g., 1.0% to 10% by weight, based on the total weight of the composition.

In some embodiments, a dental hygiene product, e.g., toothpaste, comprises an anti-caries agent such as a soluble fluoride source capable of providing free fluoride ions, while in some embodiments a fluoride source is not included. Soluble fluoride ion sources include sodium fluoride, stannous fluoride, and sodium monofluorophosphate, for example. See, e.g., U.S. Pat. Nos. 2,946,725 and 3,678,154. In some embodiments, fluoride ion source is provided in an amount sufficient to provide between 50 and 3500 ppm, e.g., between 500 and 1500 ppm, fluoride ions. A non-fluoride anti-caries agent (e.g., anti-bacterial agent) may be included or not. Other ingredients that may be present in some embodiments or specifically excluded include a bicarbonate ion source, a pyrophosphate ion source (e.g., pyrophosphate salt), buffering agent(s), coloring or or pacifying agent(s) (e.g., titanium dioxide), a stabilizer, and preservative(s) (e.g., parabens). Representative examples of various dental hygiene product formulations, ingredients, and methods of preparation are found, for example, in PCT/US1997/021157 (WO/1998/023250) FLAVOR SYSTEMS FOR ORAL CARE PRODUCTS and in Weinert, W., "Oral Hygiene Products", Ullmann's Encyclopedia of Industrial Chemistry, Wiley-VCH, Weinheim, 2000. One of ordinary skill in the art would readily select ingredient(s) and formulation approaches that are compatible with each other (e.g., do not significantly reduce the capacity of an ingredient to produce the intended effect). One of ordinary skill in the art will appreciate that some ingredients may serve multiple functions (e.g., sorbitol may serve as a sweetener and humectant) and that various categories of ingredient may be omitted or other categories may be included. The invention contemplates "natural" toothpastes that are essentially devoid of artificially synthesized compounds that do not occur in nature.

The toothpaste or dental cream of this invention is typically prepared by conventional methods of making toothpastes and/or dental creams or dental gels (with the proviso that an allergen is incorporated into the composition). More specifically, for example, in some embodiments the gelling agent such as a cellulose gum is dispersed in glycerine, to which is added an aqueous solution containing the sweetening agent such as xylitol, followed by the addition of sorbitol and mixing for a period of about 20 minutes to hydrate the gum, mixing the gum mixture with the polishing agent in a mixer under a vacuum of 28-30 inches of pressure. Lastly, the flavor, the surfactant and processed allergen are added to the vacuum mixer, mixed for a period of about 15 minutes, and the final mixture is placed in a tube or other container suitable for dispensing the toothpaste, such as a vertical dispenser equipped with a pump. Of course ingredients can be combined in any appropriate order compatible with the nature of the ingredients. The tube, pump, or other dispensing container may be marked to indicate that its contents include an allergen and/or to depict one or more allegen(s) or allergen source(s) and/or may feature a brand name, logo, etc. The container may be labeled with information regarding flavor, ingredients, etc. Similar considerations apply with regard to packaging, labeling of other inventive delivery forms, e.g., chewing gum, dental pick or floss, porous pouch, etc.

An ordinary use involves, for example, approximately 2 gm of toothpaste having approximately 1-10% by weight processed allergen (or other suitable amount of allergen in processed or natural form, as discussed above). In some embodiments a "pea-sized" quantity of toothpaste (e.g., 0.2 gm-0.5 gm, e.g., about 0.3 gm) may be suitable for a child between the ages of 2 and 6 years. In some embodiments, a toothpaste dispenser that dispenses a predetermined quantity (e.g., a predetermined volume) of toothpaste upon activation is used. Activation may be achieved, e.g., by pushing a button, depressing a lever, activating a motion sensor, or other approaches as known in the art.

In certain embodiments the toothpaste may be divided into portions, a first portion comprising ingredients relating to oral cleanliness and health, and a second portion comprising ingredients relating to the development of allergic tolerance. Production of multi-portioned toothpastes wherein, for example, the portions are coaxially aligned in delivery form, are well-known in the art. This product delivery form is typically employed where composition requirements vary as between the base ingredients and desired additive ingredients, or where it is desired that the ingredients of one portion remain in the oral cavity for a longer period of time. For example, whereas a portion comprising base ingredients may be hydrophilic and substantially removed by rinsing of the oral cavity with water, a second portion comprising allergenic extract may be hydrophobic and may include filming properties. In some embodiments, an inventive toothpaste is multi-striped, wherein the different stripes differ in composition. For example, one or more stripes may contain allergen while others do not. In some embodiments, a multi-cavity dispensing container that permits simultaneous coextrusion of two or more flowable materials, e.g., in a predetermined proportion, is used. See, e.g., U.S. Pat. No. 5,020,694. In some embodiments, the toothpaste has a multilayer composition. In producing such embodiments, desired toothpaste layers can be fed into the dispensing container (e.g., tube) in parallel streams to form a multilayered appearance. The dentifrice layers will be extruded in the desired multilayer configuration when dispensed from the tube.

A person of ordinary skill in the art of dental hygiene product formulation will immediately recognize how to match a composition ingredient characteristic to a formulation parameter to achieve desired effect with respect to exposure time in the oral cavity.

Unique advantages afforded by this embodiment include very high potential for full compliance by the consumer. In conventional and ordinary usage, the typical American already purchases dental hygiene products for use several times per day. Over 40 percent of Americans report that brushing teeth just prior to bedtime is a ritual or habitual activity. Hence, the enhanced exposure is accomplished as part of an already existing daily routine. In some embodiments, a daily regimen includes at least one exposure of the inventive dental hygiene product to the oral cavity (e.g., 1, 2, 3, 4, or 5 exposures) for periods ranging from 15 seconds to 10 minutes. A contemplated suitable use regimen includes exposure of the inventive dental hygiene product to the oral cavity 2-4 times per day for periods ranging from about 30 to about 90 seconds. Regimens involving less frequent use are also contemplated, e.g., 1, 2, or 3 times weekly, alternate days, etc.

The toothpaste can be applied using a typical toothbrush, e.g., a manual toothbrush comprising a head with bristles, a handle for gripping the toothbrush, and a neck portion connecting the head and the handle, or an electric toothbrush. An electric toothbrush may additionally comprise a motor and a power source (e.g., a battery-operated, optionally rechargeable) in electrical communication with the motor. In some embodiments, a toothbrush comprises a timer that produces a signal (e.g., a sound or light) after a brushing session has continued for at least a predetermined period of time. For example, the timer may produce a signal after 30, 60, 90, 120, 150, 180, 210, or 240 seconds, in various embodiments. The period of time may be selectable, e.g., by the user. Of course a timer that is separate from the toothbrush could be used, if desired. In some embodiments, the toothbrush briefly interrupts power at predetermined intervals or after a predetermined interval, e.g., any of the afore-mentioned time periods, thereby prompting the user to begin brushing a different area of the mouth.

In some embodiments, an electric toothbrush comprises one or more microprocessor(s), data storage element(s), and/or display(s). The microprocessor(s), data storage element(s) ("memory"), and display(s) can be typical components as commonly found in consumer electronic devices. The display can comprise, for example, a LCD or LED screen. The memory can store information regarding, for example, the duration, frequency, and/or other characteristic(s) of tooth brushing sessions. Such data can be displayed on the toothbrush display or on a separate display. A microprocessor, data storage element, and/or display may, for example, be located within the toothbrush, within the base unit of an electric toothbrush, or in a completely separate unit. In some embodiments, a display prompts a user to continue brushing or cease brushing and/or provides other messages to the user. PCT/US2007/023677 (WO/2008/060482—PERSONAL CARE PRODUCTS AND METHODS) discloses an illustrative oral care system comprising an electric toothbrush and a display in data communication with the electric toothbrush.

In some embodiments, a tooth brushing system, e.g., a toothbrush, serves as a dispenser for an inventive dental hygiene product and/or method. Tooth brushing systems, e.g., toothbrushes, suitable for dispensing toothpaste and/or other oral care products are known in the art. The toothbrush can comprise one or more reservoir(s) from which toothpaste and/or or other material(s) is/are dispensed prior to and/or during brushing, or a brush may be removable from a base that contains one or more reservoir(s). Dispensing can, for example, occur prior to a tooth brushing session and/or intermittently or continuously during at least part of a tooth brushing session. In some embodiments, a metered dosing pump, which may be included in the body of the toothbrush, controls the flow of toothpaste from the reservoir and through a conduit that delivers the toothpaste to the toothbrush head, e.g., to or adjacent to the bristles of the toothbrush head. Operation of the metered dosing pump dispenses a measured and controlled amount of toothpaste. In some embodiments, a first reservoir comprises toothpaste, and a second reservoir delivers additional material (e.g., an allergen preparation) to the flow of toothpaste. In some embodiments, an allergen (optionally together with one or more other components) is delivered at least in part after the toothpaste has been dispensed. The allergen preparation may, for example, be delivered to the bristles or through the toothbrush head. In some embodiments, conventional toothpaste is delivered from a first reservoir, and an allergen is delivered from a second reservoir. In some embodiments, a toothbrush is loadable with cartridge(s) that contain an allergen. Such allergen-containing cartridges suitable for inserting into a toothbrush or using to load a toothbrush with an allergen preparation are an aspect of the invention. Delivery of toothpaste and/or allergen preparation may be regulated by a microprocessor, which is optionally programmable to deliver a selected amount of toothpaste and/or allergen preparation. Illustrative examples of tooth brushing systems capable of serving as a dispensing system are disclosed in PCT/US2001/043442 (WO/2002/041802—APPARATUS, METHOD AND PRODUCT FOR TREATING TEETH) and PCT/US2008/054695 (WO/2008/103892—TOOTHBRUSH WITH INTEGRATED TOOTHPASTE DELIVERY. A toothpaste packaged as a dual chambered container is disclosed in Soparkar P., et al., J Clin Dent. 15(2):46-51, 2004.

In some aspects, the invention provides a dental floss or dental pick that delivers a composition comprising an allergen and/or is used to promote contact of a composition of the invention with the oral mucosa (e.g., gingival and/or vestibular mucosa). In some embodiments, a dental pick comprises multiple flexible bristles (e.g., rubber bristles) that, for example, slide between teeth to remove plaque and food particles, while promoting circulation by massaging and stimulating the gingiva. For example, the dental pick may have about 50-100 bristles, e.g., about 70-80 bristles. In some embodiments, a user applies a dental hygiene product of the invention (e.g., toothpaste, oral gel) to the oral mucosa (e.g., gingviva and/or vestibulum) and/or to the bristles of the dental pick. Use of the dental pick distributes the composition and promotes contact with the oral mucosa. An exemplary dental pick is the GUM® Soft-Pick® (Sunstar Americas, Inc.).

In some embodiments, a dental floss comprises bundle of thin filaments (e.g., nylon filaments) or fibres, or a plastic (e.g., Teflon or polyethylene) ribbon of use to remove food and dental plaque from teeth. In some embodiments a dental floss may be flavored or unflavored, and coated or uncoated (e.g., waxed or unwaxed). Dental floss may be provided in a dispenser or dental floss pick, for example. In some embodiments, a dental floss comprises an allergen impregnated into a coating layer (e.g., a wax) or distributed as an outer layer of a coating layer. In some embodiments, an allergen is encapsulated, e.g., microcapsules or nanocapsules. In some embodiments, encapsulation helps in stabilizing and/or preserving the potency of allergen, e.g., during manufacture and/or storage of the dental floss. In some embodiments, allergen desorbs or is otherwise released from the coating and/or microcapsules as the dental floss is used. Suitable materials for encapsulating active agents are known in the art and include a wide variety of different synthetic and naturally occurring polymers. In some embodiments, release of allergen is promoted by mechanical action of flossing between teeth and/or by contact with water and/or saliva in the mouth, e.g., by enzymatic action, e.g., of enzymes in saliva.

In some embodiments, a dental pick or dental floss is packaged or otherwise sold or marketed together with an inventive dental hygiene product (e.g., a toothpaste, gel, etc.). Such packages are within the scope of the invention.

Another specific embodiment directed to providing a composition according to the invention in very convenient and familiar delivery mode include application by use of an oral gel. This embodiment is particularly suitable for night time exposure as salivation decreased substantially at night, and the gel does not present the choking hazard inherent to solid delivery forms. Hence, in a very specific embodiment the gel is applied to the vestibular mucosal surface just prior to sleeping. In some embodiments, the gel is applied at least in part to the buccal mucosa just prior to sleeping. In other specific embodiments, the gel is provided in the form of a gel plug. The gel plug is designed to fit in any of several nooks of the vestibular region.

In a further specific embodiment, the sustained exposure is provided by an oral strip comprising the one or more allergens, wherein the oral strip comprises a hydrophilic polymer that dissolves with exposure to saliva. According to this embodiment, the oral strip may be applied to the vestibular mucosal surface just prior to sleeping or until it fully dissolves. Guidance for production of suitable oral strips in accordance with the instant invention is provided, for example, in R. P. Dixit et al. 'Oral Strip Technology: Overview and Future Potential' J. Controlled Release 139 (2009) 94-107, the disclosure of which is incorporated herein by this reference. Dixit teaches suitable formulation parameters and exemplifies additives which may considered including sweetening, flavoring, coloring, stabilizing and thickening agents and saliva stimulating agents. Manufacturing concerns including strip-forming polymers, thickness, industry tests, tensile strength, elongation, tear and fold parameters, dissolution and disintegration control factors are all addressed therein.

The invention provides chewing gums comprising one or more allergens. In general, a chewing gum of the invention may be produced using conventional ingredients and methods for manufacturing chewing gums, with appropriate modifications to incorporate one or more allergens. One of ordinary skill in the art is aware of appropriate ingredients and formulation methods for chewing gums. For example, a chewing gum may contain a gum base comprising chicle, a natural latex product, other natural gums, or a synthetic rubber (e.g., polyisobutylene). Typically chewing gum contains one or more flavoring agents, to impart a flavor such as mint, wintergreen, cinnamon, etc., and may contain sweetening agent (s). Ingredients can include one or more humectants, softeners, coloring agents, stabilizers, preservative, etc. A chewing gum may have film-forming characteristics for blowing bubbles. Chewing gum can be manufactured in a variety of shapes such as sticks, ribbons, balls, etc. In some embodiments, a chewing gum is coated or glazed, e.g., with a suitable wax. In some embodiments, a gum is a center-filled gum, e.g., a pellet or ball gum formed around a soft or liquid center. In some embodiments, an allergen is provided in such center. Optionally, the center is surrounded at least in part by a barrier layer. Suitable barrier layers may comprise, e.g., a wax. See, e.g., US patent application publication 20060263476 (CENTER-FILLED CHEWING GUM WITH BARRIER LAYER). In general, the amount of allergen to be incorporated into a stick of chewing gum can be as described above for pouch or dental hygiene product. In some embodiments, a typical use entails chewing 1-5 units (sticks, balls, etc.) of chewing gum daily. Regimens involving less frequent use are also contemplated, e.g., 1, 2, or 3 times weekly, alternate days, etc. In some embodiments, a typical use entails chewing 1-10 units of chewing gum weekly.

In some aspects, the invention provides a method of making a dental hygiene composition (e.g., toothpaste, mouthwash, dental cream), the method comprising: a) providing base ingredients for said dental hygiene composition; and b) combining at least one allergen with said base ingredients. In some embodiments, the method further comprises (c) placing said dental hygiene composition in a container suitable for dispensing the composition. In some embodiments, the method comprises providing the at least one allergen in a form that has been quantified with regard to allergen content. The allergen may, for example, have been quantified based on a reference standard. In some embodiments, the method comprises providing the at least one allergen in an amount appropriate to result in a predetermined minimum and/or maximum amount of allergenic protein and/or predetermined minimum and/or maximum number of allergen units, e.g., on a volume or weight basis of the dental hygiene composition. In some embodiments, a method comprises testing the dental hygiene composition, e.g., to determine the amount of allergen in the composition, e.g., to confirm that the composition comprises at least a predetermined minimum amount of allergen and/or that the amount of allergen does not exceed a predetermined maximum amount, e.g., on a volume or weight basis of the dental hygiene composition. In some aspects, the invention provides dental hygiene composition and methods of making thereof, wherein the dental hygiene composition has batch to batch consistency with regard to allergen content.

In some aspects, similar methods are provided for making a chewing gum of the invention. In some embodiments, an allergen comprises a protein, and the allergen is substantially the only protein ingredient included in the dental hygiene composition or chewing gum. In some embodiments, an allergen comprises a protein, and the allergen is structurally distinct from any ingredients that may be conventionally used in a dental hygiene composition or chewing gum.

In some embodiments of any aspect of the invention (e.g., dental hygiene product such as toothpaste; dental pick or dental floss composition for inclusion in porous pouch, chewing gum), an allergen can be associated with microparticles. For example, the allergen can be encapsulated by such particles and/or microparticles can be impregnated or coated or otherwise physically associated with allergen. "Microparticle" as used herein, encompasses any microscopic particles used to protect and/or deliver agents in areas such as pharmaceuticals, nutraceuticals, cosmeceuticals, cosmetics, food technology, and the like. Such particles may be referred to in the art as microcapsules, microspheres, nanospheres, nanoparticles, nanocapsules, liposomes, and the like. Methods of making and employing such delivery systems are well known in the art. Examples are described, e.g., in references such as: Lakkis, J M (ed.) Encapsulation and controlled release technologies in food systems (Wiley-Blackwell, 2007); Nedovic, V. and Zuuidam, N J (eds.) (Springer, 2009); Cohen, S. and Bernstein, H. Microparticulate systems for the delivery of proteins and vaccines (CRC Press, 1996); Jones, D., Pharmaceutical Applications of Polymers for Drug Delivery (ChemTec Publishing, 2004). Benita, S. (ed.) Microencapsulation: methods and industrial applications (Informa Healthcare; $2^{nd}$ ed., 2005), all of which are incorporated by reference. In some aspects, known approaches used in substances expected to contact the oral cavity (e.g., foods) are used in the present invention. A number of polymeric delivery vehicles for providing sustained release are known in the art. One of ordinary skill would select appropriate polymers for use in various embodiments of the invention. In some embodiments, a biocompatible polymer, which may be biodegradable, may be used. The polymers may be homopolymers, copolymers (including block copolymers), straight, branched-chain, or cross-linked. Natural or synthetic polymers can be used in various embodiments of the invention. Polymers include, but are not limited to, poly-lactic acid (PLA), poly-glycolic acid (PGA), poly-lactide-co-glycolide (PLGA), poly(phosphazine), poly (phosphate ester), polycaprolactones, polyanhydrides, ethylene vinyl acetate, polyorthoesters, polyethers, and poly (beta amino esters). Other polymers include polyamides, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, poly(methyl methacrylate), poly(ethyl methacrylate), poly(butylmethacrylate), poly (isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene, polyvinylpyrrolidone, poly(butyric acid), poly(valeric acid), and poly(lactide-cocaprolactone). Peptides, polypeptides, proteins such as collagen or albumin, polysaccharides such as sucrose, chitosan, dextran, alginate, hyaluronic acid (or derivatives or combinations of any of these), dendrimers (e.g., PAMAM dendrimers), dextrins, cyclodextrins may be used in various embodiments. Methods for preparation of such formulations will be apparent to those skilled in the art. Liposomes or other lipid-containing particles can be used in some embodiments. Exemplary polymers include cellulose derivatives such as, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxymethylcellulose, carboxylethyl cellulose, cellulose triacetate, cellulose sulphate sodium salt, polycarbamates or polyureas, Chemical derivatives of the afore-mentioned polymers, e.g., substitutions, additions of chemical groups, for example, alkyl, alkylene, hydroxylations, oxidations, and other modifications routinely made by those skilled in the art can be used.

In some embodiments of the invention, a composition for use in a delivery form of the invention (e.g., a pouch or a dental hygiene product or chewing gum) contains one or more allergen(s) of relevance to a particular geographic area. For example, the allergen(s) can be allergen(s) of plants (e.g., pollen allergens) that grow commonly in such area, and/or allergen(s) of fungi, insects, mites, etc., that are commonly found in such area. In some embodiments, a composition for use in a delivery form of the invention (e.g., a pouch or a dental hygiene product) contains one or more allergen(s) that are significant causes of allergy in a geographical area. In some embodiments, an allergen is a significant cause of allergy if it is among the 5 most commonly diagnosed allergy-causing agents in a particular category (e.g., airborne, ingested, skin contact) in a geographical area. Diagnosis may be based on, e.g., skin prick testing or other methods accepted in the art. A geographical area can be a continent, e.g., North America, South America, Europe, Asia, Africa, Australia; one or more countr(ies), regions, or jurisdictions (e.g., US, Canada, Mexico, Argentina, Brazil, Chile, Venezuela, European Union, Belgium, Denmark, France, Germany, Italy, Netherlands, Norway, Poland, Spain, Sweden, Switzerland, United Kingdom, Turkey, Russia, Eurasia, Israel, Japan, China, Korea, India, Pakistan, Philippines, Singapore, Vietnam, Thailand, Indonesia, Egypt, South Africa, ARIPO member state(s), Australia, etc.) or portion(s) thereof (e.g., one or more states or provinces). A geographical region can be defined based at least in part on climate or other natural features. In some embodiments a geographical area is at least 10,000 km$^2$ in area. In some embodiments, a dental hygiene product of the invention is formulated to have one or more characteristic(s) (e.g., flavor, color, texture, etc.) that closely match those of a dental hygiene product that is familiar to at least some people living in a particular geographic area that corresponds to the allergen(s) in the inventive dental hygiene product, e.g., a dental hygiene product that is marketed in such area. In some aspects, the invention provides methods of making a dental hygiene composition comprising a) providing base ingredients for said dental hygiene composition; and b) combining at least one allergen with said base ingredients, wherein the at least one allergen is relevant to a selected geographical area. In some embodiments the base ingredient(s) and/or amount(s) thereof are selected such that characteristic(s) of the resulting composition are familiar to at least some people living in such geographic area.

In some embodiments of the various aspects of the invention, a subject is an individual who has a history of allergy symptoms and/or who has received a diagnosis of allergy. In some embodiments, a subject is at risk of developing an allergy. In some embodiments a subject who has a family history of allergy is at risk of developing an allergy. In some embodiments, a subject has a positive skin prick test or skin patch test to one or more allergen(s). In some embodiments, a subject has detectable serum IgE (as assessed, e.g., using RAST) against one or more allergen(s). In some embodiments, a subject who has detectable serum IgE, e.g., abnormally high levels of serum IgE (as assessed, e.g., using RAST) against an allergen is at risk of developing an allergy to that allergen (or to other allergens that share cross-reactive epitopes.) As known in the art RAST (radioallergosorbent test) is a radioimmunoassay test used to detect specific IgE antibodies to suspected or known allergens. Since IgE is the antibody associated with Type I allergic response, if a subject exhibits a significant level of IgE directed against an allergen, the test may indicate that the subject is allergic to such allergen (or to allergens that share epitopes with the allergen) or is at risk of developing an allergy to the allergen (or to allergens that share epitopes with the allergen). Other methods of detecting allergen-specific IgE are known in the art.

As known in the art, many allergens are immunologically cross-reactive with other allergens, e.g., allergens that share at least some similar or identical epitopes (e.g., IgE antibodies that bind to a first allergen will also bind to allergens that share at least some similar or identical epitopes). Thus an individual who is allergic to an allergen from a first species will often be allergic to other allergens, e.g., allergens from related species. In some embodiments, a first allergen may be used to desensitize a subject to a second allergen. The first and second allergens may be derived from different sources. For example, in the case of allergens of plant, animal, or fungal origin, the first and second allergens may be derived from different species within a genus, or different genera within a subfamily or family, or different subfamilies within a family. For example, in some embodiments, the invention contemplates use of a pollen allergen from one or more grasses or trees of a first subfamily to desensitize individuals to pollen of one or more grasses or trees of a second subfamily. In some embodiments, the invention contemplates use of pollen allergen from trees of the subfamily Cupressoideae (e.g., junipers) to desensitize individuals to pollens of the subfamily Taxodioidea (e.g., Japanese cedar), or vice versa. For example, Japanese cedar pollen allergens can be immunologically cross reactive with allergens of *Cupressus sempervirens, Juniperus ashei, Cupressus arizonica, Cupressus macrocarpa, Juniperus virginiana, Juniperus communis, Thuya orientalis*, and/or *Chamaecyparis obtusa*.

Personalized methods for decreasing a subject's allergic response to an environmental allergen are also provided. In certain embodiments an allergen associated with a subject's allergic response is identified and a commercially available extract of the allergen is procured. The extract is mixed with, for example, an organic non-toxic filler material. A flexible porous pouch according to the invention is filled with the mixture, wherein the filled pouch is suitable for insertion by the subject into an oral cavity of the subject and capable of fixedly conforming to a vestibular mucosal surface of the oral cavity, and inserting the pouch so that it fixedly conforms to the vestibular mucosal surface. It is contemplated that the identified allergen derives from the subject's environment and is suspected of causing undesirable clinical symptoms in the subject. In very specific embodiments the subject may be able to avoid the prospect of having to eliminate a pleasurable source of the offending allergen, for example a pet, by tailoring vestibular immunotherapy with respect to the particular pet.

Any of the aspects, embodiments, and features of the invention can be freely combined, and such combinations are within the scope of the invention. For example, in some aspects, the invention contemplates use of multiple different inventive delivery forms by a subject. For example, a subject may use an inventive pouch containing an allergen during an induction phase and a dental hygiene product, e.g., a toothpaste, for maintenance. Inventive delivery forms can also be used together with SLIT or other forms of immunotherapy. For example, a subject may initiate desensitization with SLIT and switch to use of an inventive delivery form for maintenance.

In general, a subject could start on a regimen of using an inventive pouch, dental hygiene product, or chewing gum at any time. In some embodiments, it is contemplated that a subject starts on a regimen of using an inventive pouch, dental hygiene product, or chewing gum at least 7 days prior to an anticipated exposure to an allergen. For example, a subject may commence using an inventive pouch, dental hygiene product, or chewing gum at least 1-4 weeks, 4-8 weeks, 8-16 weeks, 16-24 weeks, 24-36 weeks, or 36-52 weeks prior to an anticipated exposure, etc. "Rush" regimens and "ultra-rush" regimens are also contemplated. In a "rush regimen", a subject is exposed to successively increasing amount of allergen spaced over a relatively short period of time such as about 8 hours to 7 days. In an "ultra-rush" regimen, a subject is exposed to successively increasing amount of allergen separated by short time intervals, such as 30 minutes, over a period of about 2-8 hours. An anticipated exposure may be, for example, the typical beginning of pollen season, a planned trip to a location where the allergen occurs in the environment, acquisition of a pet, etc. The subject may continue using inventive pouches or dental hygiene products during the period of exposure to the allergen. In some embodiments, a subject uses an inventive product prior to and during multiple seasonal exposures to an allergen, e.g., a pollen. In some embodiments, a pre-coseasonal protocol is used, which starts every year approximately 4 months before the pollen season and is continued throughout the season (approximately 1 to 2 months depending on the country and regions) and then is stopped at the end of the season. This will be repeated each year approximately 4 months before the pollen season in accordance with the same protocol. In some embodiments, a perennial protocol is used, which can be started at any time (e.g., at least 4 months before the pollen season) and typically involves regular use (e.g., daily, weekly, etc.) continuously throughout the course of use. In some embodiments, the overall duration of use is 3 to 5 years or 3 to 5 consecutive seasons in the case of the pre-coseasonal protocol. In some embodiments, it is contemplated that the subject continues to use inventive pouches or dental hygiene products indefinitely. In some embodiments, a protocol includes an induction phase that involves escalating the amount of delivered allergen over a period of time to reach a maintenance dose level.

Any of the inventive delivery forms or compositions may be packaged or otherwise provided together with instructions, e.g., relating to suitable use regimens, amounts, etc.

In some embodiments, an inventive pharmaceutical composition (e.g., a composition for inclusion in a pouch, or the pouch containing the composition, or a dental hygiene product or chewing gum) is packaged together with a label approved by a government agency responsible for regulating pharmaceutical agents, e.g., the U.S. Food & Drug Administration, or comparable agency in a different jurisdiction.

The present invention also provides kits. A kit comprising (a) a plurality of flexible porous pouches suitable for insertion into an oral cavity of a subject and capable of fixedly conforming to a vestibular mucosal surface of the oral cavity, the pouches comprising a composition comprising at least one allergen. and (b) instructions comprising a dosing schedule effective for desensitizing the subject to the at least one allergen thereby reducing the severity of at the clinical symptoms.

In some embodiments, the invention provides a kit comprising: a plurality of flexible porous pouches as described herein; a plurality of individually contained extracts of a set of common environmental allergens; an amount of organic non-toxic filler material; and instructions for mixing extract with the filler material and for filling the flexible porous pouch.

In some embodiments, the invention provides a kit as described herein, wherein the composition of the set of common environmental allergens is based on the environment of the subject.

If desired, the effect of the inventive allergen immunotherapy products with regard to desensitizing a subject can be assessed using methods known in the art for assessing symptoms and/or signs of allergy. In some embodiments, an effective amount is an amount that decreases (ameliorates, reduces, etc.) one or more symptoms or manifestations of allergy and/or decreases likelihood of developing one or more symptoms or manifestations of allergy (or associated conditions such as asthma, atopic dermatitis) upon exposure to an allergen, e.g., as compared with the level of such symptom(s) or manifestation(s) expected or previously experienced by a subject in the absence of using an inventive composition or product of the invention. For example, subject becomes significantly less sensitive to the allergen than previously the case, or than would be expected based, for example, on the subject's history. In some embodiments, a reduction in symptoms is clinically significant, e.g., as assessed by a medical practitioner familiar with the allergic condition. One of ordinary skill in the art would be aware of symptoms and manifestations of allergic conditions. Typical allergy symptoms (e.g., to airborne allergens) include, for example, sneezing, rhinorrhoea, nasal congestion, nasal and ocular pruritus (itching), and tearing. Further details regarding symptoms, diagnosis, etc., are described in standard textbooks such as Adkinson, N F, et al., Middleton's Allergy: Principles and Practice, $7^{th}$ edition (Mosby, 2008) Symptoms can be scored, optionally using any of a variety of instruments known in the art for assessing allergy severity and/or for assessing efficacy of agents or procedures for alleviating allergic manifestations. For example, in some embodiments, the Rhinoconjunctivitis Total Symptom Score (RTSS), a sum of 6 individual symptom scores for sneezing, runny nose, itchy nose, nasal congestion, watery eyes, and itchy eyes is used. See, e.g., Wahn U, et al., J Allergy Clin Immunol., 123(1):160-166, 2009, incorporated by reference. In some embodiments, the Japanese Allergic Rhinitis Quality of Life (QOL) Standard Questionnaire No. 1 (JRQLQ No. 1) (Okubo, supra) may be used. One of ordinary skill in the art will appreciate that many different scoring systems suitable assessing allergy symptoms could be employed. Use of rescue medications (e.g., antihistamines) can be monitored, wherein a reduction in the requirement for rescue medications is indicative of a beneficial effect resulting from use of an inventive product. Other methods of assessing efficacy include performing an antigen challenge test, e.g., by skin exposure (e.g., skin prick), respiratory exposure, ingestion, etc., and assessing response thereto as compared, for example, with response prior to embarking on a regimen of using an inventive pouch or dental hygiene product. Appropriate statistical test(s) (e.g., t-test, Chi-square test, ANOVA, etc.) known to those of ordinary skill in the art can be used to demonstrate a statistically significant benefit, e.g., reduction in one or more symptoms, reduction in total score on a standardized instrument, reduction in use of rescue medications, etc., achieved by using an inventive product. In some embodiments, statistical significance refers to a p value of <0.05. In some embodiments, statistical significance refers to a p value of <0.01.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. It will be appreciated that the invention is in no way dependent upon particular results achieved in any specific example or with any specific embodiment. Articles such as "a", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims or from the description above is introduced into another claim. For example, any claim that is dependent on another claim can be modified to include one or more elements, limitations, clauses, or descriptive terms, found in any other claim that is dependent on the same base claim. Furthermore, where the claims recite a composition, it is to be understood that methods of using the composition for any of the purposes disclosed herein are included within the scope of the invention, and methods of making the composition according to any of the methods of making disclosed herein are included within the scope of the invention, unless otherwise indicated or unless it would be evident to one of ordinary skill in the art that a contradiction or inconsistency would arise. Methods can include a step of providing a subject having an allergy or being at risk of developing an allergy or allergic reaction, a step of diagnosing a subject as having an allergy or being at risk of developing an allergy or allergic reaction, and/or a step of selecting a subject for which an inventive product or method would be suitable.

Where elements are presented as lists, it is to be understood that each subgroup of the elements is also disclosed, and any element(s) can be removed from the group. For purposes of conciseness only some of these embodiments have been specifically recited herein, but the invention includes all such embodiments. It should also be understood that, in general, where the invention, or aspects of the invention, is/are referred to as comprising particular elements, features, etc., certain embodiments of the invention or aspects of the invention consist, or consist essentially of, such elements, features, etc.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Any particular embodiment, aspect, element, feature, etc., of the present invention, or any combination thereof, may be explicitly excluded from any one or more claims whether or not such exclusion is expressly recited herein. For example, any allergen or ingredient, etc., can be explicitly excluded. Applicants reserve the right to proviso out of the claims any specific allergen, allergen category, ingredient, ingredient category, or combination thereof, whether or not such allergen, ingredient, category, or combination thereof, is recited herein. To the extent, if any, that a dental hygiene product, chewing gum product, or a composition for use in a pouch that is known or described in the prior art may include an allergen, the instant invention may be distinguished from such prior art product or composition in, for example, any one or more of the following ways: (i) the product or composition of the invention comprises one or more allergen(s) not present in the prior art product or composition; (ii) the product or composition of the invention comprises a different amount of allergen, or a different form of the allergen, than present in the prior art composition; (iii) the product or composition of the invention explicitly excludes the allergen(s) present in the prior art product or composition; (iv) the composition of the invention comprises at least one ingredient not present in the prior art product composition or present in a different amount and/or omits at least one ingredient present in the prior art product or composition.

The invention claimed is:

1. A method for decreasing sensitivity or for maintaining decreased sensitivity to one or more allergens and reducing symptoms of allergy in a subject, the method comprising: applying a toothpaste composition in accordance with a dental hygiene regimen comprising tooth-brushing so as to result in contact of the allergen with the vestibular mucosa of the subject, said toothpaste composition formulated to comprise at least one allergen provided in natural form, as an extract of the allergen, or in a recombinantly produced form of the allergen.

2. The method according to claim 1, wherein the toothpaste composition comprises a mixture of: a) toothpaste base ingredients; and b) the at least one allergen comprising an allergenic protein provided in natural form or as an extract of the allergen, or in a recombinantly produced form.

3. The method according to claim 2, wherein the at least one allergen is selected from the group consisting of a plant pollen allergen, an allergen that is immunologically cross-reactive with a plant pollen allergen, an animal allergen, a fungal allergen, an allergen that is immunologically cross-reactive with an animal allergen, a food allergen, an allergen that is immunologically cross-reactive with a food allergen, an allergen that is immunologically cross-reactive with a fungal allergen, and combinations thereof.

4. The method according to claim 3, wherein the at least one allergen is a plant pollen allergen or an allergen that is immunologically cross-reactive with a plant pollen allergen, or a combination thereof.

5. The method according to claim 4, wherein the plant pollen allergen comprises one or more grass pollen allergens.

6. The method according to claim 5, wherein the one or more grass pollen allergens are derived from a grass within the *Dactylis, Poa, Lolium, Anthoxantum, Phleum, Festuca, Agrostis* or *Cynodon* genus of grasses.

7. The method according to claim 6, wherein the allergen comprises a *Poa* a, *Poa* p or Phl p protein.

8. The method according to claim 7, wherein the allergen is selected from a group consisting of *Poa* a 1 protein, *Poa* p 5 protein, and combinations thereof.

9. The method according to claim 4, wherein the plant pollen allergen is selected from one or more of the Asteraceae, Amaranthaceane, Urticaceae, Euphorbiaceae, and Plantaginacceae families.

10. The method according to claim 9, wherein the plant pollen allergen is an Amb a protein, an Art v protein, an Ole e-like protein, a Pla 1 protein, a Par j protein or combinations thereof.

11. The method according to claim allergen 3, wherein the at least one allergen comprises a dust mite allergen.

12. The method according to claim 11, wherein the at least one allergen comprises a Def p protein, a Der f protein, a Tyr p protein, or combinations thereof.

13. The method according to claim 3, wherein the at least one allergen comprises a combination of two or more allergens selected from the group consisting of a plant pollen allergen, a mite allergen, an insect allergen, a mold allergen, and an animal dander allergen.

14. The method according to claim 13, wherein the plant pollen allergen comprises a ragweed allergen and the mite allergen comprises a dust mite allergen.

15. The method according to claim 2, wherein the toothpaste composition is personalized to the subject, the composition comprising at least one allergen selected from allergens identified as triggering or potentially triggering an allergic response in the subject.

16. The method according to claim 15, wherein an allergen identified as triggering or potentially triggering an allergic response in the consumer derives from an animal.

17. The method according to claim 2, wherein the toothpaste composition is formulated to comprise at least two portions including a first substantially hydrophilic portion comprising the toothpaste base ingredients and a second substantially hydrophobic portion comprising the at least one allergen.

18. The method according to claim 1, further comprising providing the formulated toothpaste composition in a toothpaste dispensing device.

19. The method according to claim 1, wherein the at least one allergen comprising an allergenic protein is provided as a glycerinated formulation comprising the allergen.

20. A method for decreasing or maintaining a decrease in a subject's allergic response to an environmental allergen comprising: identifying an allergen present in the subject's environment and associated with the allergic response; formulating a toothpaste to comprise the identified allergen or an extract of the identified allergen, and applying the toothpaste to an oral cavity of the subject in accordance with a dental hygiene regimen comprising tooth-brushing so as to result in contact of the allergen with the vestibular mucosa of the subject.

* * * * *